US012065645B2

(12) United States Patent
Gong et al.

(10) Patent No.: US 12,065,645 B2
(45) Date of Patent: Aug. 20, 2024

(54) REVERSE TRANSCRIPTASES AND USES THEREOF

(71) Applicant: Bio-Rad Laboratories, Inc., Hercules, CA (US)

(72) Inventors: Xiao-Song Gong, Hercules, CA (US); Yan Wang, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 18/125,661

(22) Filed: Mar. 23, 2023

(65) Prior Publication Data

US 2023/0332142 A1 Oct. 19, 2023

Related U.S. Application Data

(60) Continuation of application No. 17/211,595, filed on Mar. 24, 2021, now Pat. No. 11,649,453, which is a division of application No. 15/895,504, filed on Feb. 13, 2018, now Pat. No. 10,988,762.

(60) Provisional application No. 62/459,974, filed on Feb. 16, 2017.

(51) Int. Cl.

| | |
|---|---|
| ***C12N 9/12*** | (2006.01) |
| ***C12N 9/22*** | (2006.01) |
| ***C12N 15/10*** | (2006.01) |
| ***C12Q 1/686*** | (2018.01) |
| *C12Q 1/6844* | (2018.01) |

(52) U.S. Cl.

CPC ........... *C12N 15/1096* (2013.01); *C12N 9/22* (2013.01); *C12Q 1/686* (2013.01); *C12N 2770/00022* (2013.01); *C12Q 1/6844* (2013.01)

(58) Field of Classification Search

None

See application file for complete search history.

(56) References Cited

U.S. PATENT DOCUMENTS

| | | | |
|---|---|---|---|
| 5,244,797 | A | 9/1993 | Kotewicz et al. |
| 5,405,776 | A | 4/1995 | Kotewicz et al. |
| 5,668,005 | A | 9/1997 | Kotewicz et al. |
| 6,721,004 | B1 | 4/2004 | Kato |
| 7,595,179 | B2 | 9/2009 | Chen et al. |
| 8,361,754 | B2 | 1/2013 | Chen et al. |
| 8,753,845 | B2 | 6/2014 | Dhariwal et al. |
| 8,956,841 | B2 | 2/2015 | Chen et al. |
| 2014/0286907 | A1 | 9/2014 | Sarkis et al. |
| 2014/0363854 | A1 | 12/2014 | Smith et al. |
| 2016/0194678 | A1 | 7/2016 | Martin et al. |
| 2017/0159032 | A1 | 6/2017 | Gong |

FOREIGN PATENT DOCUMENTS

| | | |
|---|---|---|
| EP | 0377842 A1 | 7/1990 |

OTHER PUBLICATIONS

International Search Report and Written Opinion from PCT/US2018/017977 mailed May 23, 2018; 9 pages.

Stewart, H. et al.; "Complete genome sequences of two feline leukemia virus subgroup B isolates with novel recombination sites"; Genome Announcements; vol. 1, No. 1; Jan. 15, 2013; 2 pages.

Operario, D.J. et al.; "Comparison of DNA polymerase activities between recombinant feline immunodeficiency and leukemia virus reverse transcriptases"; *Virology*; vol. 335; 2005; pp. 106-121.

Misra, H.S. et al.; "An Enzymatically Active Chimeric HIV-1 Reverse Transcriptase (RT) with the RNase-H Domain of Murine Leukemia Virus RT Exists as a Monomer"; *The Journal of Biological Chemistry*; vol. 273, No. 16; Apr. 17, 1998; pp. 9785-9789.

Tanese, N. et al.; "Domain structure of the Moloney murine leukemia virus reverse transcriptase: Mutational analysis and separate expression of the DNA polymerase and RNase H activities"; *Proc. Natl. Acad. Sci. USA*; vol. 85; Mar. 1988; pp. 1777-1781.

Das, D. et al.; "The Crystal Structure of the Monomeric Reverse Transcriptase from Moloney Murine Leukemia Virus"; *Structure*; vol. 12; May 2004, pp. 819-829.

Arezi, B. et al.; "Novel mutations in Moloney Murine Leukemia Virus reverse transcriptase increase thermostability through tighter binding to template-primer"; Nucleic Acids Research; vol. 37, No. 2; 2009; pp. 473-481.

Baranauskas, A. et al.; "Generation and characterization of new highly thermostable and processive M-MuLV reverse transcriptase variants"; Protein Engineering, Design & Selection; vol. 25, No. 10; Jun. 12, 2012; pp. 657-668.

Blain, S.W. et al.; "Differential Effects of Moloney Murine Leukemia Virus Reverse Transcriptase Mutations on RNase H Activity in Mg2+ and Mn2+"; The Journal of Biological Chemistry; vol. 271, No. 3; Jan. 19, 1996; pp. 1448-1454.

Skirgaila, R. et al.; "Compartmentalization of destabilized enzyme-mRNA-ribosome complexes generated by ribosome display: a novel tool for the directed evolution of enzymes"; Protein Engineering, Design & Selection; vol. 26, No. 78; May 10, 2013; pp. 453-461.

Extended European Search Report in EP Appln. 18754654.4 mailed Oct. 19, 2020; 9 pages.

Sharma, S.K. et al.; "Engineering of the human-immunodeficiency-virus-type-1 (HIV-1) reverse transcriptase gene to prevent dimerization of the expressed chimaeric protein: Purification and characterization of a monomeric reverse-transcriptase"; Biotechnology and Applied Biochemistry; vol. 19, No. 1; Jan. 1, 1994; pp. 155-167.

Yasukawa, K. et al.; "Characterization of Moloney Murine Leukaemia Virus/Avian Myeloblastosis Virus Chimeric Reverse Transcriptases"; Journal of Biochemistry; vol. 145, No. 3; Jan. 4, 2009; pp. 315-324.

*Primary Examiner* — Richard G Hutson

(74) *Attorney, Agent, or Firm* — Kilpatrick Townsend and Stockton LLP

(57) ABSTRACT

Hybrid reverse transcriptases formed from portions of FLVRT and MLVRT are provided.

17 Claims, 1 Drawing Sheet

Specification includes a Sequence Listing.

RT mutant expression analysis
soluble fraction on SDS-PAGE gel
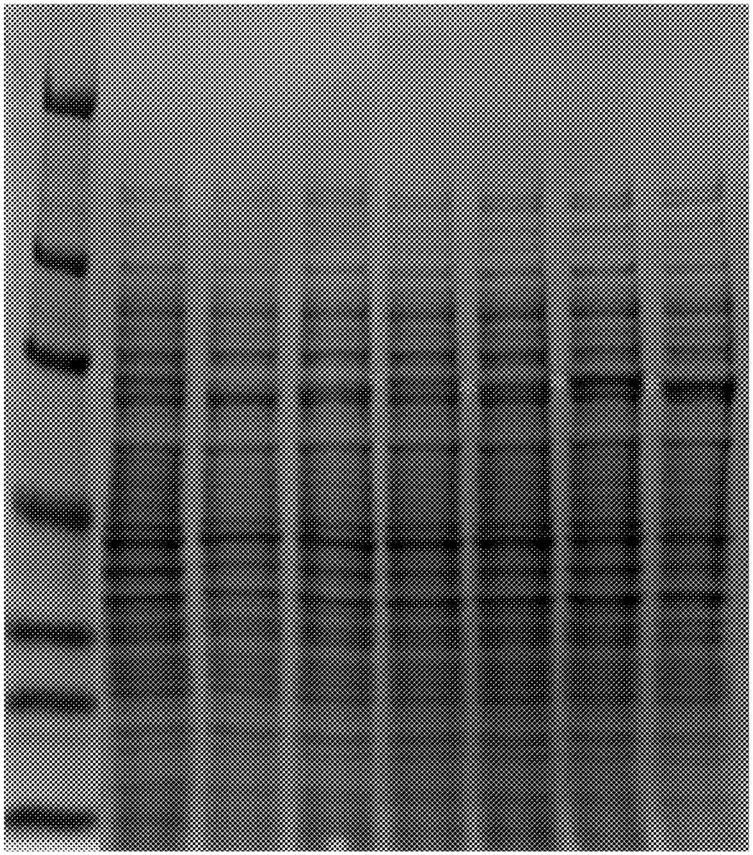
1. Wt MLV RT
2. Truncated FLV RT
3. Wt FLV RT
4. FM1 (1/3F 2/3M)
5. FM2 (2/3F 1/3M)
6. MF (1/3M 2/3F)
7. MFP (1/3M 2/3F)
*: indicates the expressed recombinant RT band.

REVERSE TRANSCRIPTASES AND USES THEREOF

CROSS-REFERENCE TO RELATED PATENT APPLICATIONS

The present patent application is a continuation of U.S. patent application Ser. No. 17/211,595, filed Mar. 24, 2021, which is a divisional of U.S. patent application Ser. No. 15/895,504, filed Feb. 13, 2018, which claims benefit of priority to U.S. Provisional Patent Application No. 62/459,974, filed on Feb. 16, 2017, each of which is incorporated by reference for all purposes.

REFERENCE TO A SEQUENCE LISTING

The instant application contains a Sequence Listing which has been submitted electronically in XML format and is hereby incorporated by reference in its entirety. Said XML copy, created on May 9, 2023, is named 094260-1380552_112730US_SL.xml and is 82,492 bytes in size.

BACKGROUND OF THE INVENTION

The detection, analysis, transcription, and amplification of nucleic acids are frequently-used procedures in modern molecular biology. DNA polymerases are useful for detection and amplification of DNA or RNA. The application of such procedures for RNA analysis can involve the investigation of gene expression, diagnosis of infectious agents or genetic diseases, and the generation of cDNA, to name but a few applications. The reverse transcription of RNA thus has many uses. In some instances, the reverse transcriptase is followed by polymerase chain reaction amplification which can be used for rapid detection and quantification of RNA.

BRIEF SUMMARY OF THE INVENTION

In some embodiments, a hybrid reverse transcriptase is provided comprising a finger domain, a palm domain, a thumb domain, a connection domain and an RNase H domain, wherein at least one of said domains is a mouse leukemia virus reverse transcriptase (MLVRT) and other of said domains are from feline leukemia virus reverse transcriptase (FLVRT).

In some embodiments, the hybrid reverse transcriptase comprises: a portion of mouse leukemia virus reverse transcriptase (MLVRT) comprising finger and palm domains linked to a portion of feline leukemia virus reverse transcriptase (FLVRT) comprising thumb, connection, and RNase H domains. In some embodiments, the portion of the MLVRT has a carboxyl terminus and the carboxyl terminus is linked directly to an amino terminus of the portion of the FLVRT. In some embodiments, the portion of the MLVRT has a carboxyl terminus and the carboxyl terminus is linked to an amino terminus of the portion of the FLVRT via a linking amino acid sequence of 1-100 amino acids. In some embodiments, the portion of the MLVRT is at least 95% identical to SEQ ID NO:1 and the portion of the FLVRT is at least 95% identical to SEQ ID NO:5.

In some embodiments, the portion of the MLVRT comprises SEQ ID NO:1 and the portion of the FLVRT comprises SEQ ID NO:5. In some embodiments, the portion of the FLVRT comprises SEQ ID NO:6 or SEQ ID NO:10. In some embodiments, the portion of the FLVRT comprises SEQ ID NO:7, SEQ ID NO:8, SEQ ID NO:9, or SEQ ID NO:11.

In some embodiments, the portion of the MLVRT comprises SEQ ID NO:2. In some embodiments, the portion of the MLVRT comprises SEQ ID NO:3 or SEQ ID NO:4.

In some embodiments, the portion of the MLVRT comprises SEQ ID NO:4 and the portion of the FLVRT comprises SEQ ID NO:7; or the portion of the MLVRT comprises SEQ ID NO:4 and the portion of the FLVRT comprises SEQ ID NO:8; or the portion of the MLVRT comprises SEQ ID NO:4 and the portion of the FLVRT comprises SEQ ID NO:9; or the portion of the MLVRT comprises SEQ ID NO:3 and the portion of the FLVRT comprises SEQ ID NO:11; or the portion of the MLVRT comprises SEQ ID NO:3 and the portion of the FLVRT comprises SEQ ID NO:10; or the portion of the MLVRT comprises SEQ ID NO:4 and the portion of the FLVRT comprises SEQ ID NO:13.

In some embodiments, the hybrid reverse transcriptase comprises a sequence substantially (e.g., at least 70%, 80%, 85%, 90%, or 95%) identical to SEQ ID NO: 14, 15, 16, 17, 18, 19, 34, or 35.

In some embodiments, the hybrid reverse transcriptase comprises a portion of feline leukemia virus reverse transcriptase (FLVRT) comprising finger and palm domains linked to a portion of mouse leukemia virus reverse transcriptase (MLVRT) comprising RNase H domains. In some embodiments, the portion of MLVRT comprises thumb, connection, and RNase H domains. In some embodiments, the portion of FLVRT comprises a sequence at least 95% identical to SEQ ID NO:26; and the portion of MLVRT comprises a sequence at least 95% identical to SEQ ID NO:28. In some embodiments, the hybrid reverse transcriptase comprises a sequence substantially (e.g., at least 70%, 80%, 85%, 90%, or 95%) identical to SEQ ID NO:30.

In some embodiments, the portion of FLVRT comprises finger, palm, thumb and connection domains. In some embodiments, the portion of FLVRT comprises a sequence substantially (e.g., at least 70%, 80%, 85%, 90%, or 95%) identical to SEQ ID NO:27; and the portion of MLVRT comprises a sequence substantially (e.g., at least 70%, 80%, 85%, 90%, or 95%) identical to SEQ ID NO:29. In some embodiments, the hybrid reverse transcriptase comprises a sequence substantially (e.g., at least 70%, 80%, 85%, 90%, or 95%) identical to SEQ ID NO:31.

In some embodiments, the hybrid reverse transcriptase as described above or elsewhere herein has at least one mutation that improves thermostability. In some embodiments, the at least one mutation at a position corresponding to L139, D200, N479, D522, F526, H592, L601, E605, and H632 in SEQ ID NO:34.

Also provided is a nucleic acid comprising a polynucleotide encoding the hybrid reverse transcriptase as described above or elsewhere herein. In some embodiments, the nucleic acid further comprises a (optionally heterologous) promoter operably linked to the polynucleotide.

Also provided is an expression vector comprising the nucleic acid as described above or elsewhere herein. Also provided is a cell comprising the expression vector. In some embodiments, the cell is a bacterial cell.

Also provided is a reaction mixture comprising: an RNA or DNA template; and the hybrid reverse transcriptase as described above or elsewhere herein. In some embodiments, the reaction mixture further comprises at least one oligonucleotide primer and/or deoxynucleotides.

Also provided is a method of performing reverse transcription. In some embodiments, the method comprises contacting the hybrid reverse transcriptase as described above or elsewhere herein in a reaction mixture with a template RNA and a primer that hybridizes to the template RNA under conditions such that the hybrid reverse transcriptase extends the primer in a template RNA-dependent manner to form a cDNA In some embodiments, the conditions comprise an extension step between 42-60° C.

Also provided is a kit comprising the hybrid reverse transcriptase as described above or elsewhere herein. In some embodiments, the kit further comprises a DNA polymerase.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

"Heterologous", when used with reference to portions of a protein, indicates that the protein comprises two or more domains that are not found in the same relationship to each other in nature. Such a protein, e.g., a fusion protein such as the hybrid RTs described herein, contains two or more sequences covalently linked via a peptide bond or peptide linker sequence arranged to make a new functional protein.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

"Polymerase" refers to an enzyme that performs template-directed synthesis of polynucleotides. The term encompasses both the full length polypeptide and a domain that has polymerase activity.

A "template" refers to a polynucleotide sequence that comprises the polynucleotide to be amplified, optionally flanked by one or two primer hybridization sites.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, . gamma.-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region or when not specified the whole sequence (SEQ ID NO)), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Percent sequence identity and sequence similarity is determined using the BLAST® algorithm, which is described in Altschul et al., J. Mol. Biol. 215:403-410 (1990). Software for performing BLAST® analyses is publicly available through the National Center for Biotechnology Information (http://www.ncbi.nlm.nih.go-v/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLAST® program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

BRIEF DESCRIPTION OF THE DRAWINGS

FIG. 1 depicts an exemplary soluble fraction SDS-PAGE gel following RT mutant expression.

DETAILED DESCRIPTION OF THE INVENTION

The inventors have discovered that reverse transcriptase (RT) hybrids formed from a mouse leukemia virus reverse transcriptase (MLVRT) and feline leukemia virus reverse transcriptase (FLVRT) have improved solubility compared to FLVRT enzymes. The hybrids described herein are also expected to have improved stability, expression, or a combination thereof compared to at least one of non-hybrid MLVRT or FLVRT enzymes. For example, the inventors have generated hybrid reverse transcriptases comprising a finger domain, a palm domain, a thumb domain, a connection domain and an RNase H domain, wherein at least one of said domains is a mouse leukemia virus reverse transcriptase (MLVRT) and other of said domains are from feline leukemia virus reverse transcriptase (FLVRT). As discussed in more detail, the inventors have generated hybrids in which the finger and palm domains are either FLVRT or MLVRT sequences with at least some of the remainder being from the alternative enzyme.

Polypeptides

Provided herein are hybrid reverse transcriptases (RTs) that have the five RT domains (from amino to carboxyl: finger, palm, thumb, connection, and RNase H domains) where at least one (e.g., 1, 2, 3, or 4) of those domains are from MLVRT and the remaining domain(s) are from FLVRT. The structure of MLVRT and finger, palm, thumb, connection, and RNase H domains are described in, e.g., Das and Georgiadis, Structure 12:819-829 (2004). The resulting hybrid RTs have improved expression (e.g., in *E. coli*) compared to an RT where all of the domains are from FLVRT (i.e., wildtype FLVRT) while in some embodiments having improved accuracy compared to MLVRT.

MLV-FLV Hybrids

In some embodiments, the hybrid RT comprises the finger and palm domains of MLVRT linked to the thumb, connection, and RNase H domains of FLVRT. Exemplary portions of MLVRT that comprise finger and palm domains include, for example, SEQ ID NO:1 or a substantially identical sequence thereof. In some embodiments, the portion of MLVRT that comprises finger and palm domains comprises SEQ ID NO:2 or a sequence substantially identical thereto. The above-described MLVRT portion can be linked to a portion of FLVRT that comprises the thumb, connection, and RNase H domains. An exemplary portion of FLVRT that comprises the thumb, connection, and RNase H domains is SEQ ID NO: 5 or a substantially identical sequence thereof. In some embodiments, the portion of FLVRT that comprises the thumb, connection, and RNase H domains is SEQ ID NO: 6 or a substantially identical sequence thereof or SEQ ID NO:10 or a substantially identical sequence thereof. Exemplary hybrid RTs can comprise, for example SEQ ID NO:1 or SEQ ID NO:2 any of SEQ ID NO:5, SEQ ID NO:6, or SEQ ID NO:10. In some embodiments, the hybrid RT comprises one of SEQ ID NOs: 14, 15, 16, 17, 18, or 19 or a substantially identical sequence thereof.

FLV-MLV Hybrids

In some embodiments, the hybrid RT comprises at least the finger and palm domains of FLVRT linked to the thumb and connection domains of either FLVRT or MLVRT, which in turn is linked to the RNase H domains of MLVRT. In some embodiments, the hybrid RT comprises finger and palm domains of FLVRT and thumb, connection, and RNase H domains of MLVRT. Exemplary portions of FLVRT that comprise finger and palm domains include, for example, SEQ ID NO:26 or a substantially identical sequence thereof. Exemplary portions of MLVRT that comprise thumb, connection, and RNase H domains include, for example, SEQ ID NO:28 or a substantially identical sequence thereof.

In some embodiments, the hybrid RT comprises finger, palm, thumb, and connection domains of FLVRT and RNase H domain of MLVRT. Exemplary portions of FLVRT that comprise finger, palm, thumb, and connection domains include, for example, SEQ ID NO:27 or a substantially identical sequence thereof. Exemplary portions of MLVRT that comprise the RNase H domain include, for example, SEQ ID NO:29 or a substantially identical sequence thereof. In some embodiments, the hybrid RT comprises one of SEQ ID NO: 30 or 31, or a substantially identical sequence thereof.

Any of the hybrid RTs described herein can include further amino acids at the amino or carboxyl terminus. Exemplary additional amino acid sequences can include, for example, epitope tags or other tags that allow for purification of the proteins or whose underlying codons allow for cloning sites. Such tags can be fused at either end of the hybrid RT as most convenient for purification. Examples of such tags include, but are not limited to poly-histidine sequences or FLAG-tag. Various linker sequences can also be include to link such tags or other sequences to the hybrid RT sequence. Linkers can include, for example glycine, serine or other amino acids that do not significantly interfere with protein folding such that the activity of the hybrid RT is not harmed. The linker sequences can also include protease cleavage sequences such that the tag can be removed by a protease or other cleavage mechanism, optionally once the hybrid RT has been purified (e.g., using the tag). In some embodiments, the hybrid RT includes one or more (e.g., 2-20, 2-5, e.g., 3) alanines at the carboxyl terminus.

Thermostable Mutations

As noted herein, any hybrid RTs as described herein can include one or more mutation that improves the thermostability (i.e., ability to remain active during or after exposure to temperatures over 37° C., e.g., 42-60° C.) of the enzyme. Exemplary mutations include one or more (e.g., 2, 3, 4, 5, 6, or more) mutation at a position corresponding to L139 (including but not limited to L139P), D200 (including but not limited to D200N), N479 (including but not limited to N479D), D522 (including but not limited to, D522G, D522N, or D522A), F526 (including but not limited to F5261), H592 (including but not limited to H592K), L601 (including but not limited to L601W), E605 (including but not limited to E605K), and H632 (including but not limited to H632Y) in SEQ ID NO:34. It should be understood that such position designations do not indicate the number of amino acids in the claimed molecule per se, but indicate where in the claimed molecule the residue occurs when the claimed molecule sequence is maximally aligned with SEQ ID NO:34.

Linking of Portions

Two portions of different RTs as described herein as described can be joined via a linker by methods well known to those of skill in the art. These methods can include either recombinant and chemical methods.

Linking portions of different RTs may also comprise a peptide bond formed between moieties that are separately synthesized by standard peptide synthesis chemistry or recombinant methods. Alternatively, in some embodiments, the coding sequences of each portion in the hybrid RT are directly joined and expressed as a fusion protein. Alternatively, an amino acid linker sequence may also be encoded in the polypeptide coding sequence and employed to separate the first and second RT portions by a distance sufficient to ensure that each polypeptide folds into its secondary and tertiary structures. Such an amino acid linker sequence is incorporated into the fusion protein using recombinant techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences are not necessarily required.

Chemical linking can be performed, for example, as described in Bioconjugate Techniques, Hermanson, Ed., Academic Press (1996). Joining can include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages. Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Alabama. These linkers optionally have amide linkages, sulfhydryl linkages, or heterobifunctional linkages. The linking group can be a chemical crosslinking agent, including, for example, succinimidyl-(N-maleimidomethyl)-cyclohexane-1-carboxylate (SMCC). The linking group can also be an additional amino acid sequence(s), including but not limited to, for example, a polyalanine, polyglycine or similarly, linking group.

In some embodiments, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N-methyl amino acids, and amino acid analogs in general. Furthermore, the amino acid can be D (dextrorotary) or L (levorotary).

Expression and Purification

Nucleic acids encoding the hybrid RTs can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117, each of which is incorporated by reference in its entirety for all purposes and in particular for all teachings related to amplification methods.

One of skill will recognize that modifications can additionally be made to the hybrid RTs without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The hybrid RT polypeptides as described herein can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, Gene Expression in Recombinant Microorganisms (Bioprocess Technology, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus*, and Pyricularia. See, e.g., U.S. Pat. No. 5,679,543 and Stahl and Tudzynski, Eds., Molecular Biology in Filamentous Fungi, John Wiley & Sons, 1992. Synthesis of heterologous proteins in yeast is well known and described in the literature. Methods in Yeast Genetics, Sherman, F., et al., Cold Spring Harbor Laboratory, (1982) is a well-recognized work describing the various methods available to produce the enzymes in yeast.

There are many expression systems for producing the polypeptides that are well known to those of ordinary skill in the art. (See, e.g., Gene Expression Systems, Fernandex and Hoeffler, Eds. Academic Press, 1999; Sambrook and Russell, supra; and Ausubel et al, supra.) Typically, the polynucleotide that encodes the polypeptide is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived PL promoter and N-gene ribosome binding site (Shimatake et al., Nature (1981) 292: 128). The particular promoter system is not critical; any available promoter that functions in prokaryotes and provides the desired level of activity can be used. Standard bacterial expression vectors include plasmids such as pBR322-based plasmids, e.g., pBLUESCRIPT™, pSKF, pET23D, lambda-phage derived vectors, and fusion expression systems such as GST and LacZ. Epitope tags can also be added to recombinant proteins to provide convenient methods of isolation, e.g., c-myc, HAtag, 6-His tag, maltose binding protein, VSV-G tag, anti-DYKDDDDK (SEQ ID NO:42) tag, or any such tag, a large number of which are well known to those of skill in the art.

The polypeptides described herein can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2: 800; Schoner et al., Bio/Technology (1985) 3: 151). Polypeptides can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the polypeptides, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., "FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

After biological expression or purification, the hybrid RT polypeptide(s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem. 268: 14065-14070; Kreitman and Pastan (1993) Bioconjug. Chem. 4: 581-585; and Buchner et al. (1992) Anal. Biochem. 205: 263-270). Debinski et al., for example, describe the denaturation and reduction of inclusion body proteins in guanidine-DTE. The protein is then refolded in a redox buffer containing oxidized glutathione and L-arginine.

V. Methods of Use

Reverse transcription (RT) is an amplification method that copies RNA into DNA. RT reactions can be performed with reaction mixtures as described herein. For example, the invention provides for reverse transcribing one or more RNA (including for example, all RNA in a cell, e.g., to make a cDNA library) under conditions to allow for reverse transcription using a hybrid RT as described herein and generation of a first and optionally second strand cDNA. The RT reaction can be primed with a random primer, an oligo dT, or an RNA-specific primer. Components and conditions for RT reactions are generally known.

If desired, the reactions can further comprise RT-PCR. Standard techniques for performing PCR assays are known in the art (PCR Technology: Principles and Applications for DNA Amplification (Erlich, ed., 1989); PCR Protocols: A Guide to Methods and Applications (Innis, Gelfland, Sninsky, &, White, eds., 1990); Mattila et al., Nucleic Acids Res. 19: 4967 (1991); Eckert & Kunkel, PCR Methods and Applications 1: 17 (1991); Wallace et al., Ligase Chain Reaction, in Technologies for Detection of DNA Damage and Mutations, pp. 307-322 (Pfiefer, ed., 1996)). RT and PCR reactions are often used in the same assay and are referred to as RT-PCR. RT-PCR combines reverse transcription of RNA into DNA and subsequent DNA amplification reactions in a single reaction. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., Molecular Cloning: A Laboratory Manual (2nd ed.) (1989); Ausubel, F. M. et al., eds. (1999) Short Protocols in Molecular Biology, 4th edition, John Wiley & Sons); Ausubel, F. M. et al., eds. (1999-2010) Current Protocols in Molecular Biology, John Wiley & Sons).

In some embodiments, hybrid RTs described herein are used in a reverse transcriptase reaction at a higher temperature than would ordinarily be used. Thus, in embodiments, the some hybrid RTs described herein can be used at, 37° or 42° C., or a temperature greater than 42° C., for example, between 42°-60°, 43°-55°, 45°-56°, 45°-65° C., etc. Higher temperature RT reactions are particularly helpful in situations where the template RNA forms secondary structure at normal RT temperatures (e.g., 37° or 42° C.) that partially or completely inhibit reverse transcription.

VI. Reaction Mixtures

Reaction mixtures comprising the hybrid RT polypeptides described herein are provided. The reaction mixtures can comprise, for example, a target nucleic acid, e.g., an RNA target where reverse transcription is to take place. The reaction mixtures can comprise appropriate nucleotides (e.g., deoxynucleotides (dNTPs) or dideoxynucleotides) and in some embodiments, at least one buffer. Exemplary buffers can include, for example and without limitation, Tris, HEPES, ACES, PIPES, MOPSO, BES, MOPS, TES, TAPSO, POPSO, BICINE, TAPS, or AMPSO. The reaction mixtures can optionally comprise one or more oligonucleotides that function as a primer for template-dependent nucleic acid extension, one or more oligonucleotides that function as a probe (e.g., linked to a label such as a quencher, fluorescent dye, etc.), and/or a double stranded DNA binding dye (e.g., SYBRGREEN). In some embodiments, the reaction mixture will further comprises a separate DNA-dependent DNA polymerase. In some embodiments, the reaction mixture will further comprises magnesium (Mg++).

VII. Kits

In one aspect, kits for conducting reverse transcription (and optionally cyclic amplification, e.g., such as PCR) reactions are provided. In some embodiments, such kits include a hybrid RT as described herein, and optionally dNTPs, and at least one buffer. Such kits may also include stabilizers and other additives to increase the efficiency of the amplification reactions. Such kits may also include one or more primers (e.g. poly-T, random hexamers, or specific primers) as well as instructions for conducting reverse transcription reactions using the components of the kits. In some embodiments, the kits will further comprises a separate DNA-dependent DNA polymerase.

EXAMPLES

In order to increase the recombinant FLV RT solubility in *E. coli* cells, hybrid RTs were constructed with part of the RT polypeptide sequence from MLV RT, and part of the RT sequence from FLV RT. Hybrid RT constructs made exhibited improved solubility in *E. coli* cells as demonstrated in FIG. 1.

The hybrid RT FM1 (⅓ FLV-⅔ MLV RT) included a N-terminal sequence of FLV RT from amino acid 1-279, which includes the finger and palm domains, and a C-terminal sequence of MLV RT from amino acid 280-671, which includes the thumb, connection and RNase H domain.

The hybrid RT FM2 (⅔ FLV-⅓ MLV RT) included a N-terminal sequence of FLV RT from amino acid 1-497, which includes the finger, palm, thumb, and connection domains, and a C-terminal sequence of MLV RT from amino acid 498-671, which includes the RNase H domain.

The hybrid RT MF includes a N-terminal sequence of MLV RT from amino acid 1-277, which includes the finger and palm domains, and a C-terminal sequence of FLV RT from amino acid 276-667, which includes the thumb, connection, and RNase H domains.

The hybrid RT MF(P) includes a N-terminal sequence of MLV RT from amino acid 1-221, which includes the finger and palm domains, and a C-terminal sequence of FLV RT from amino acid 221-667, which includes the thumb, connection, and RNase H domains.

Point mutations were introduced into MF and MF(P) hybrid RTs in order to improve the enzyme performance.

Method of Expression of Recombinant RT Constructs:

Fresh LB broth was inoculated with overnight culture of BL21 cells containing 5 expression plasmids in a ratio of 100:1. The cultures were grown at 25° C. for about 6 hr or until OD600 nm=0.6-0.8. IPTG was added to 0.1 mM, and grown 0/N for 16 hrs at 16° C. Cells were harvested by collecting the pellet after centrifugation. Cells were resuspended in 200 ml lysis buffer and lysed by sonication. The cell debris was spun down and 200 μl of supernatant was collected. 5 μl sample and 5 μl loading buffer were combined in a PCR strip and heated at 95° C. for 5 min. 6ul of the samples were loaded onto an SDS-PAGE gel for analysis. Exemplary results are shown in FIG. 1.

The hybrid and mutant proteins were tested for a number of characteristics, which is summarized in part in the following table (blanks indicate the activity was not tested):

| | Thermostability | Reaction Speed | Processivity | Expression Level |
|---|---|---|---|---|
| MF5PNAIYC | ++++ | | | ++++ |
| MF5PNAIY | ++++ | ++++ | ++++ | ++++ |
| MF4GC | ++++ | | | ++++ |
| MF4G | ++++ | ++++ | ++++ | ++++ |
| MF(P)4GC | ++++ | | | ++++ |
| MF(P)4G | ++++ | +++ | ++++ | ++++ |
| FF4G | +++ | ++++ | ++++ | ++ |
| FF4GC | +++ | | | ++ |
| MF6PAIKYC | ++++ | | | ++++ |
| FF4NDKW | ++ | +++ | + | ++ |
| MF(P)4NDKW | ++ | ++++ | ++ | ++++ |
| MF3AIY | +++ | ++++ | ++++ | ++++ |
| MF4CH | ++++ | ++++ | ++++ | ++++ |
| FF4CH | +++ | ++++ | ++ | ++ |
| FF4C | +++ | ++++ | ++ | ++ |
| MF(P)4C | ++++ | ++++ | +++ | ++++ |
| FF4NGWN | ++ | ++++ | ++ | ++ |
| MF(P)4NGWN | ++ | ++++ | ++ | ++++ |
| MD524G | +++ | ++++ | ++++ | ++++ |

MF(P)4C, FF4C: All "C" at the end represents an additional 15 amino acid C-terminus native sequence from FLV RT.
MF4CH, FF4CH: The "H" at the end represents a histidine Tag at the C-terminus in addition to a N-terminus His-Tag.
FF4G, FF4GC "FF" represents Feline RT mutants not the fusion between MLV and FLV RT.
FF4NDKW, MF(P)4NDKW FLV RT and Fusion RT that have 4 point mutations at D200N, N477D, H592K, L601W.
FF4NGWN, MF(P)4NGWN FLV RT and Fusion RT that have 4 point mutations at D200N, D522G, L601W, D651N.

A listing of exemplary mutant and hybrid sequences is provided below:

1. NF5PNAIY
Based on FP(M)-TCH(F), which has finger and palm domains from MLV RT and thumb, connection and RNase H domain from FLV RT. Amino acids at the following positions were mutated: L139P(160), D200N(221), D522A(543), F526I(547), H632Y(653). Italics indicate sequence from MLV; bolded text indicates sequence from FLV.

(SEQ ID NO: 20)

MGSSHHHHHHSSGLVPRGSH*MTLNIEDEYRLHETSKEPDVSLGSTWLSDFPQAWAETGGM*

*GLAVRQAPLIIPLKATSTPVSIKQYPMSQEARLGIKPHIQRLLDQGILVPCQSPWNTPLLPVKKP*

*GTNDYRPVQDLREVNKRVEDIHPTVPNPYNLLSGPPPSHQWYTVLDLKDAFFCLRLHPTSQP*

*LFAFEWRDPEMGISGQLTWTRLPQGFKNSPTLFNEALHRDLADFRIQHPDLILLQYVDDLLL*

*AATSELDCQQGTRALLQTLGNLGYRASAKKAQICQKQVKYLGYLLKEGQ*RWLTKARKEAI

LSIPVPKNPRQVREFLGTAGYCRLWIPGFAELAAPLYPLTRPGTLFQWGTEQQLAF

ENIRKALLSSPALGLPDITKPFELFIDENSGFAKGVLVQKLGPWKRPVAYLSKKLDT

-continued

VASGWPPCLRMVAAIAILVKDAGKLTLGQPLTILTSHPVEALVRQPPNKWLSNAR

MTHYQAMLLDAERVHFGPTVSLNPATLLPLPSGKPPRLSPDLAETMAQTDLTDQP

LPDADLTWYTAGSSFIRNGERKAGAAVTTESEVIWAASLPPGTSAQRAELIALTQAL

KMAKGKKLTVYTDSRYAFATAHVHGEIYRRRGLLTSEGKEIKNKNEILALLEALFL

PKRLSIIHCPGHQKGDSPQAKGNRLADDTAKKAATETQSSLTILAAA

2. MF4GC
Based on FP(M)-TCH(F), which has finger and palm domains from MLV RT and thumb, connection and RNase H domain from FLV RT with an extended C-terminal sequence. Amino acids at the following positions were mutated: L139P(160), D200N(221), D522G(543), L601W(622), E605K(626). Italics indicate sequence from MLV; bolded text indicates sequence from FLV.

(SEQ ID NO: 21)

MGSSHHHHHHSSGLVPRGSH_MTLNIEDEYRLHETSKEPDVSLGSTWLSDFPQAWAETGGM_

_GLAVRQAPLIIPLKATSTPVSIKQYPMSQEARLGIKPHIQRLLDQGILVPCQSPWNTPLLPVKKP_

_GTNDYRPVQDLREVNKRVEDIHPTVPNPYNLLSGPPPSHQWYTVLDLKDAFFCLRLHPTSQP_

_LFAFEWRDPEMGISGQLTWTRLPQGFKNSPTLFNEALHRDLADFRIQHPDLILLQYVDDLLL_

_AATSELDCQQGTRALLQTLGNLGYRASAKKAQICQKQVKYLGYLLKEGQ_RWLTKARKEAI

LFAFEWRDPEMGISGQLTWTRLPQGFKNSPTLFNEALHRDLADFRIQHPDLILLQYVDDLLL

ENIRKALLSSPALGLPDITKPFELFIDENSGFAKGVLVQKLGPWKRPVAYLSKKLDT

VASGWPPCLRMVAAIAILVKDAGKLTLGQPLTILTSHPVEALVRQPPNKWLSNAR

MTHYQAMLLDAERVHFGPTVSLNPATLLPLPSGKPPRLSPDLAETMAQTDLTDQP

LPDADLTWYTGGSSFIRNGERKAGAAVTTESEVIWAASLPPGTSAQRAELIALTQA

LKMAKGKKLTVYTDSRYAFATAHVHGEIYRRRGWLTSKGKEIKNKNEILALLEAL

FLPKRLSIIHCPGHQKGDSPQAKGNRLADDTAKKAATETQSSLTILPTELIEGPKRP

PWEYAAA

3. MF4G
Based on FP(M)-TCH(F), which has finger and palm domains from MLV RT and thumb, connection and RNase H domain from FLV RT without an extended C-terminal sequence. Amino acids at the following positions were mutated: L139P(160), D200N(221), D522G(543), L601W(622), E605K(626). Italics indicate sequence from MLV; bolded text indicates sequence from FLV.

(SEQ ID NO: 22)

MGSSHHHHHHSSGLVPRGSH_MTLNIEDEYRLHETSKEPDVSLGSTWLSDFPQAWAETGGM_

_GLAVRQAPLIIPLKATSTPVSIKQYPMSQEARLGIKPHIQRLLDQGILVPCQSPWNTPLLPVKKP_

_GTNDYRPVQDLREVNKRVEDIHPTVPNPYNLLSGPPPSHQWYTVLDLKDAFFCLRLHPTSQP_

_LFAFEWRDPEMGISGQLTWTRLPQGFKNSPTLFNEALHRDLADFRIQHPDLILLQYVDDLLL_

_AATSELDCQQGTRALLQTLGNLGYRASAKKAQICQKQVKYLGYLLKEGQ_RWLTKARKEAI

LSIPVPKNPRQVREFLGTAGYCRLWIPGFAELAAPLYPLTRPGTLFQWGTEQQLAF

ENIRKALLSSPALGLPDITKPFELFIDENSGFAKGVLVQKLGPWKRPVAYLSKKLDT

VASGWPPCLRMVAAIAILVKDAGKLTLGQPLTILTSHPVEALVRQPPNKWLSNAR

MTHYQAMLLDAERVHFGPTVSLNPATLLPLPSGKPPRLSPDLAETMAQTDLTDQP

LPDADLTWYTGGSSFIRNGERKAGAAVTTESEVIWAASLPPGTSAQRAELIALTQA

LKMAKGKKLTVYTDSRYAFATAHVHGEIYRRRGWLTSKGKEIKNKNEILALLEAL

FLPKRLSIIHCPGHQKGDSPQAKGNRLADDTAKKAATETQSSLTILAAA

4. MF(P)4G
Based on FP(M)$^{PstI}$-TCH(F), which has a shorter finger and palm domains sequence from MLV RT compared to MF4G. The thumb, connection and RNase H domains from FLV RT without an extended C-terminal sequence. Amino acids at the following positions were -continued mutated: L139P(160), D200N(221), D522G(543), L601W(622), E605K(626). Italics indicate sequence from MLV; bolded text indicates sequence from FLV.

(SEQ ID NO: 23)

MGSSHHHHHHSSGLVPRGSH*MTLNIEDEYRLHETSKEPDVSLGSTWLSDFPQAWAETGGM*

*GLAVRQAPLIIPLKATSTPVSIKQYPMSQEARLGIKPHIQRLLDQGILVPCQSPWNTPLLPVKKP*

*GTNDYRPVQDLREVNKRVEDIHPTVPNPYNLLSGPPPSHQWYTVLDLKDAFFCLRLHPTSQP*

*LFAFEWRDPEMGISGQLTWTRLPQGFKNSPTLFNEALHRDLADFRIQHPDLILLQ*YVDDLL

LAAATRTECLEGTKALLETLGNKGYRASAKKAQICLQEVTYLGYSLKDGQRWLT

KARKEAILSIPVPKNPRQVREFLGTAGYCRLWIPGFAELAAPLYPLTRPGTLFQWG

TEQQLAFENIRKALLSSPALGLPDITKPFELFIDENSGFAKGVLVQKLGPWKRPVAY

LSKKLDTVASGWPPCLRMVAAIAILVKDAGKLTLGQPLTILTSHPVEALVRQPPNK

WLSNARMTHYQAMLLDAERVHFGPTVSLNPATLLPLPSGKPPRLSPDLAETMAQT

DLTDQPLPDADLTWYTGGSSFIRNGERKAGAAVTTESEVIWAASLPPGTSAQRAELI

ALTQALKMAKGKKLTVYTDSRYAFATAHVHGEIYRRRGWLTSKGKEIKNKNEILA

LLEALFLPKRLSIIHCPGHQKGDSPQAKGNRLADDTAKKAATETQSSLTILAAA

5. MF(P)4NDKW

Based on $FP(M)^{PstI}$-TCH(F), which has a shorter finger and palm domains sequence from MLV RT compared to MF4G. The thumb, connection and RNase H domains from FLV RT without an extended C-terminal sequence. Amino acids at the following positions were mutated: D200N(221), N479D(500), H592K(613), L601W(622). Italics indicate sequence from MLV; bolded text indicates sequence from FLV.

(SEQ ID NO: 24)

MGSSHHHHHHSSGLVPRGSH*MTLNIEDEYRLHETSKEPDVSLGSTWLSDFPQAWAETGGM*

*GLAVRQAPLIIPLKATSTPVSIKQYPMSQEARLGIKPHIQRLLDQGILVPCQSPWNTPLLPVKKP*

*GTNDYRPVQDLREVNKRVEDIHPTVPNPYNLLSGLPPSHQWYTVLDLKDAFFCLRLHPTSQP*

*LFAFEWRDPEMGISGQLTWTRLPQGFKNSPTLFNEALHRDLADFRIQHPDLILLQ*YVDDLL

LAAATRTECLEGTKALLETLGNKGYRASAKKAQICLQEVTYLGYSLKDGQRWLT

KARKEAILSIPVPKNPRQVREFLGTAGYCRLWIPGFAELAAPLYPLTRPGTLFQWG

TEQQLAFENIRKALLSSPALGLPDITKPFELFIDENSGFAKGVLVQKLGPWKRPVAY

LSKKLDTVASGWPPCLRMVAAIAILVKDAGKLTLGQPLTILTSHPVEALVRQPPNK

WLSNARMTHYQAMLLDAERVHFGPTVSLDPATLLPLPSGKPPRLSPDLAETMAQT

DLTDQPLPDADLTWYTDGSSFIRNGERKAGAAVTTESEVIWAASLPPGTSAQRAELI

ALTQALKMAKGKKLTVYTDSRYAFATAHVKGEIYRRRGWLTSEGKEIKNKNEILA

LLEALFLPKRLSIIHCPGHQKGDSPQAKGNRLADDTAKKAATETQSSLTILAAA

6. MF(P)4NGWN

Based on $FP(M)^{PstI}$-TCH(F), which has a shorter finger and palm domains sequence from MLV RT compared to MF4G. The thumb, connection and RNase H domains from FLV RT without an extended C-terminal sequence. Amino acids at the following positions were mutated: D200N(221), D522G(543), L601W(622), D651N(672). Italics indicate sequence from MLV; bolded text indicates sequence from FLV.

(SEQ ID NO: 25)

MGSSHHHHHHSSGLVPRGSH*MTLNIEDEYRLHETSKEPDVSLGSTWLSDFPQAWAETGGM*

*GLAVRQAPLIIPLKATSTPVSIKQYPMSQEARLGIKPHIQRLLDQGILVPCQSPWNTPLLPVKKP*

*GTNDYRPVQDLREVNKRVEDIHPTVPNPYNLLSGLPPSHQWYTVLDLKDAFFCLRLHPTSQP*

*LFAFEWRDPEMGISGQLTWTRLPQGFKNSPTLFNEALHRDLADFRIQHPDLILL*QYVDDLL

LAAATRTECLEGTKALLETLGNKGYRASAKKAQICLQEVTYLGYSLKDGQRWLT

KARKEAILSIPVPKNPRQVREFLGTAGYCRLWIPGFAELAAPLYPLTRPGTLFQWG

-continued

TEQQLAFENIRKALLSSPALGLPDITKPFELFIDENSGFAKGVLVQKLGPWKRPVAY

LSKKLDTVASGWPPCLRMVAAIAILVKDAGKLTLGQPLTILTSHPVEALVRQPPNK

WLSNARMTHYQAMLLDAERVHFGPTVSLNPATLLPLPSGKPPRLSPDLAETMAQT

DLTDQPLPDADLTWYT[illegible]GSSFIRNGERKAGAAVTTESEVIWAASLPPGTSAQRAELI

ALTQALKMAKGKKLTVYTDSRYAFATAHVHGEIYRRRG[illegible]LTSEGKEIKNKNEILA

LLEALFLPKRLSIIHCPGHQKGDSPQAKGNRLA[illegible]DTAKKAATETQSSLTILAAA

7. NF5PNAIYC
Based on FP(M)-TCH(F), which has finger and palm domains from MLV RT and thumb, connection and RNase H domain from FLV RT with an extended C-terminal sequence. Amino acids at the following positions were mutated: L139P(160), D200N(221), D522A(543), F526I(547), H632Y(653). Italics indicate sequence from MLV; bolded text indicates sequence from FLV.

(SEQ ID NO: 39)

MGSSHHHHHHSSGLVPRGSH*MTLNIEDEYRLHETSKEPDVSLGSTWLSDFPQAWAETGGM*

*GLAVRQAPLIIPLKATSTPVSIKQYPMSQEARLGIKPHIQRLLDQGILVPCQSPWNTPLLPVKKP*

*GTNDYRPVQDLREVNKRVEDIHPTVPNPYNLLSGPPPSHQWYTVLDLKDAFFCLRLHPTSQP*

*LFAFEWRDPEMGISGQLTWTRLPQGFKNSPTLFNEALHRDLADFRIQHPDLILLQYVDDLLL*

*AATSELDCQQGTRALLQTLGNLGYRASAKKAQICQKQVKYLGYLLKEGQ*RWLTKARKEAI

LSIPVPKNPRQVREFLGTAGYCRLWIPGFAELAAPLYPLTRPGTLFQWGTEQQLAF

ENIRKALLSSPALGLPDITKPFELFIDENSGFAKGVLVQKLGPWKRPVAYLSKKLDT

VASGWPPCLRMVAAIAILVKDAGKLTLGQPLTILTSHPVEALVRQPPNKWLSNAR

MTHYQAMLLDAERVHFGPTVSLNPATLLPLPSGKPPRLSPDLAETMAQTDLTDQP

LPDADLTWYTAGSSIIRNGERKAGAAVTTESEVIWAASLPPGTSAQRAELIALTQAL

KMAKGKKLTVYTDSRYAFATAHVHGEIYRRRGLLTSEGKEIKNKNEILALLEALFL

PKRLSIIYCPGHQKGDSPQAKGNRLADDTAKKAATETQSSLTILPTELIEGPKRPPW

EYAAA

8. MF4(P)GC
Based on FP(M)$^{PstI}$-TCH(F), which has a shorter finger and palm domains sequence from MLV RT compared to MF4G. The thumb, connection and RNase H domains from FLV RT with an extended C-terminal sequence. Amino acids at the following positions were mutated: L139P(160), D200N(221), D522G(543), L601W(622), E605K(626). Italics indicate sequence from MLV; bolded text indicates sequence from FLV.

(SEQ ID NO: 40)

MGSSHHHHHHSSGLVPRGSH*MTLNIEDEYRLHETSKEPDVSLGSTWLSDFPQAWAETGGM*

*GLAVRQAPLIIPLKATSTPVSIKQYPMSQEARLGIKPHIQRLLDQGILVPCQSPWNTPLLPVKKP*

*GTNDYRPVQDLREVNKRVEDIHPTVPNPYNLLSGPPPSHQWYTVLDLKDAFFCLRLHPTSQP*

*LFAFEWRDPEMGISGQLTWTRLPQGFKNSPTLFNEALHRDLADFRIQHPDLILLQ*YVDDLL

LAAATRTECLEGTKALLETLGNKGYRASAKKAQICLQEVTYLGYSLKDGQRWLT

KARKEAILSIPVPKNPRQVREFLGTAGYCRLWIPGFAELAAPLYPLTRPGTLFQWG

TEQQLAFENIRKALLSSPALGLPDITKPFELFIDENSGFAKGVLVQKLGPWKRPVAY

LSKKLDTVASGWPPCLRMVAAIAILVKDAGKLTLGQPLTILTSHPVEALVRQPPNK

WLSNARMTHYQAMLLDAERVHFGPTVSLNPATLLPLPSGKPPRLSPDLAETMAQT

DLTDQPLPDADLTWYTGGSSFIRNGERKAGAAVTTESEVIWAASLPPGTSAQRAELI

ALTQALKMAKGKKLTVYTDSRYAFATAHVHGEIYRRRGWLTSKGKEIKNKNEILA

-continued

LLEALFLPKRLSIIHCPGHQKGDSPQAKGNRLADDTAKKAATETQSSLTILPTELIE

GPKRPPWEYAAA

9. FM1 (1/3 FLV-2/3 MLV RT)
A hybrid RT with 1/3 of the N-terminal sequence from FLV RT (finger and palm domains) and the rest of $^2/_3$ of the C-terminal sequence from MLV RT (Thumb, connection, RNase H domains). Italics indicate sequence from MLV; bolded text indicates sequence from FLV.

(SEQ ID NO: 30)

MTLQLEEEYRLFEPESTQKQEMDIWLKNFPQAWAETGGMGMAHCQAPVLIQLKA

TATPISIRQYPMPHEAYQGIKPHIRRMLDQGILKPCQSPWNTPLLPVKKPGTKDYR

PVQDLREVNKRVEDIHPTVPNPYNLLSTLPPSHPWYTVLDLKDAFFCLRLHSESQLL

FAFEWRDPEIGLSGQLTWTRLPQGFKNSPTLFDEALHSDLADFRVRYPALVLLQYV

DDLLLAAATRTECLEGTKALLETLGNKGYRASAKKAQICLQEVTYLGYSLKDGQR

W*LTEARKETVMGQPTPKTPRQLREFLGTAGFCRLWIPGFAEMAAPLYPLTKTGTLFNWGPD*

*QQKAYQEIKQALLTAPALGLPDLTKPFELFVDEKQGYAKGVLTQKLGPWRRPVAYLSKKLDP*

*VAAGWPPCLRMVAAIAVLTKDAGKLTMGQPLVILAPHAVEALVKQPPDRWLSNARMTHYQA*

*LLLDTDRVQFGPVVALNPATLLPLPEEGLQHDCLDILAEAHGTRSDLTDQPLPDADHTWYTD*

*GSSFLQEGQRKAGAAVTTETEVIWARALPAGTSAQRAELIALTQALKMAEGKKLNVYTDSRYA*

*FATAHIHGEIYRRRGLLTSEGKEIKNKDEILALLKALFLPKRLSIIHCPGHQKGNSAEARGNRM*

*ADQAAREVATRETPGTSTLL*

10. FM2 (2/3 FLV-1/3 MLV RT)
A hybrid RT with 2/3 of the N-terminal sequence from FLV RT (finger, palm, thumb, connection domains) and the rest of $^1/_3$ of the C-terminal sequence from MLV RT (RNase H domain only). Italics indicate sequence from MLV; bolded text indicates sequence from FLV.

(SEQ ID NO: 31)

MTLQLEEEYRLFEPESTQKQEMDIWLKNFPQAWAETGGMGMAHCQAPVLIQLKA

TATPISIRQYPMPHEAYQGIKPHIRRMLDQGILKPCQSPWNTPLLPVKKPGTKDYR

PVQDLREVNKRVEDIHPTVPNPYNLLSTLPPSHPWYTVLDLKDAFFCLRLHSESQLL

FAFEWRDPEIGLSGQLTWTRLPQGFKNSPTLFDEALHSDLADFRVRYPALVLLQYV

DDLLLAAATRTECLEGTKALLETLGNKGYRASAKKAQICLQEVTYLGYSLKDGQR

WLTKARKEAILSIPVPKNPRQVREFLGTAGYCRLWIPGFAELAAPLYPLTRPGTLF

QWGTEQQLAFENIRKALLSSPALGLPDITKPFELFIDENSGFAKGVLVQKLGPWKR

PVAYLSKKLDTVASGWPPCLRMVAAIAILVKDAGKLTLGQPLTILTSHPVEALVRQ

PPNKWLSNARMTHYQAMLLDAERVHFGPTVSLNPATLLPLPSGKPPRLSPD*ILAEAH*

*GTRSDLTDQPLPDADHTWYTDGSSFLQEGQRKAGAAVTTETEVIWARALPAGTSAQRAELIAL*

*TQALKMAEGKKLNVYTDSRYAFATAHIHGEIYRRRGLLTSEGKEIKNKDEILALLKALFLPKRL*

*SIIHCPGHQKGNSAEARGNRMADQAAREVATRETPGTSTLL*

11. Wild type MLV RT sequence (SEQ ID NO: 32)

*TLNIEDEHRLHETSKEPDVSLGSTWLSDFPQAWAETGGMGLAVRQAPLIIPLKATSTPVSIKQY*

*PMSQEARLGIKPHIQRLLDQGILVPCQSPWNTPLLPVKKPGTNDYRPVQDLREVNKRVEDIH*

*PTVPNPYNLLSGLPPSHQWYTVLDLKDAFFCLRLHPTSQPLFAFEWRDPEMGISGQLTWTRL*

*PQGFKNSPTLFDEALHRDLADFRIQHPDLILLQYVDDLLLAATSELDCQQGTRALLQTLGNL*

*GYRASAKKAQICQKQVKYLGYLLKEGQRWLTEARKETVMGQPTPKTPRQLREFLGTAGFCRL*

*WIPGFAEMAAPLYPLTKTGTLFNWGPDQQKAYQEIKQALLTAPALGLPDLTKPFELFVDEKQ*

-continued

*GYAKGVLTQKLGPWRRPVAYLSKKLDPVAAGWPPCLRMVAAIAVLTKDAGKLTMGQPLVILA*

*PHAVEALVKQPPDRWLSNARMTHYQALLLDTDRVQFGPVVALNPATLLPLPEEGLQHNCLDI*

*LAEAHGTRPDLTDQPLPDADHTWYTDGSSLLQEGQRKAGAAVTTETEVIWAKALPAGTSAQR*

*AELIALTQALKMAEGKKLNVYTDSRYAFATAHIHGEIYRRRGLLTSEGKEIKNKDEILALLKALF*

*LPKRLSIIHCPGHQKGHSAEARGNRMADQAARKAAITETPDTSTLL*

12. Wild type FLV RT sequence (SEQ ID NO: 33)

TLQLEEEYRLFEPESTQKQEMDIWLKNFPQAWAETGGMGMAHCQAPVLIQLKAT

ATPISIRQYPMPHEAYQGIKPHIRRMLDQGILKPCQSPWNTPLLPVKKPGTKDYRP

VQDLREVNKRVEDIHPTVPNPYNLLSTLPPSHPWYTVLDLKDAFFCLRLHSESQLLF

AFEWRDPEIGLSGQLTWTRLPQGFKNSPTLFDEALHSDLADFRVRYPALVLLQYVD

DLLLAAATRTECLEGTKALLETLGNKGYRASAKKAQICLQEVTYLGYSLKDGQR

WLTKARKEAILSIPVPKNPRQVREFLGTAGYCRLWIPGFAELAAPLYPLTRPGTLF

QWGTEQQLAFENIRKALLSSPALGLPDITKPFELFIDENSGFAKGVLVQKLGPWKR

PVAYLSKKLDTVASGWPPCLRMVAAIAILVKDAGKLTLGQPLTILTSHPVEALVRQ

PPNKWLSNARMTHYQAMLLDAERVHFGPTVSLNPATLLPLPSGKPPRLSPDLAET

MAQTDLTDQPLPDADLTWYTDGSSFIRNGERKAGAAVTTESEVIWAASLPPGTSAQ

RAELIALTQALKMAKGKKLTVYTDSRYAFATAHVHGEIYRRRGLLTSEGKEIKNK

NEILALLEALFLPKRLSIIHCPGHQKGDSPQAKGNRLADDTAKKAATETQSSLTIL

Summary of Sequences:

- SEQ ID NO:1: generic Short MLV
- SEQ ID NO:2: generic Longer MLV
- SEQ ID NO:3: specific Short MLV
- SEQ ID NO:4: specific Longer MLV
- SEQ ID NO:5: generic Shorter w/o c-term extension FLV
- SEQ ID NO:6: with longer c-term extension FLV: generic
- SEQ ID NO:7: Shorter w/o c-term extension FLV: specific mutations at 522, 526, 632
- SEQ ID NO:8: with longer c-term extension FLV: specific mutations at 522, 601, 605
- SEQ ID NO:9: Shorter w/o c-term extension FLV: specific mutations at 522, 601, 605
- SEQ ID NO:10: long N-term w/o c-term extension FLV: generic
- SEQ ID NO:11: long N-term w/o c-term extension FLV: specific mutations at 522, 601, 605
- SEQ ID NO:12: long N-term w/o c-term extension FLV: specific mutations at 479, 592, 601
- SEQ ID NO:13: long N-term w/o c-term extension FLV: specific mutations at 522, 601, 651
- SEQ ID NO:14: NF5PNAIY without leader or end sequences
- SEQ ID NO:15: MF4GC without leader or end sequences
- SEQ ID NO:16: MF4G without leader or end sequences
- SEQ ID NO:17: MF4(P)G without leader or end sequences
- SEQ ID NO:18: MF(P)4NDKW without leader or end sequences
- SEQ ID NO:19: MF(P)4NGWN without leader or end sequences
- SEQ ID NO:20: NF5PNAIY with leader and end sequences
- SEQ ID NO:21: MF4GC with leader and end sequences
- SEQ ID NO:22: MF4G with leader and end sequences
- SEQ ID NO:23: MF(P)4G with leader and end sequences
- SEQ ID NO:24: MF(P)4NDKW with leader and end sequences
- SEQ ID NO:25: MF(P)4NGWN with leader and end sequences
- SEQ ID NO:26: ⅓ FLV N-terminus
- SEQ ID NO: 27 ⅔ FLV N-terminus
- SEQ ID NO:28 ⅔ MLV C-terminus
- SEQ ID NO:29 ⅓ MLV C-terminus
- SEQ ID NO:30 FM1 (⅓ FLV-⅔ MLV RT)
- SEQ ID NO:31 FM2 (⅔ FLV-⅓ MLV RT)
- SEQ ID NO: 32 Wild type MLV RT sequence
- SEQ ID NO: 33 Wild type FLV RT sequence
- SEQ ID NO:34: NF5PNAIYC without leader or end sequences
- SEQ ID NO:35: MF4(P)GC without leader or end sequences
- SEQ ID NO:36: NF5PNAIYC MLVRT portion
- SEQ ID NO:37: NF5PNAIYC FLVRT portion
- SEQ ID NO:38: MF4(P)GC MLVRT portion
- SEQ ID NO:39: MF4(P)GC FLVRT portion
- SEQ ID NO:40: NF5PNAIYC with leader and end sequences
- SEQ ID NO:41: MF4(P)GC with leader and end sequences The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCES

SEQ ID NO: 1: generic Short MLV:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGQ(L/P)PPSHQWYTVLDLKDAFFCLRLHPTSQPLFAFEWRDPE
MGISGQLTWTRLPQGFKNSPTLF(D/N)EALHRDLADFRIQHPDLILLQ SEQ ID NO: 2: generic Longer MLV:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSG(L/P)PPSHQWYTVLDLKDAFFCLRLHPTSQPLFAFEWRDPE
MGISGQLTWTRLPQGFKNSPTLF(D/N)EALHRDLADFRIQHPDLILLQYVDDLLLAATSE
LDCQQGTRALLQTLGNLGYRASAKKAQICQKQVKYLGYLLKEGQ SEQ ID NO: 3: specific Short MLV:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQ SEQ ID NO: 4: specific Longer MLV:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQYVDDLLLAATSELDCQQ
GTRALLQTLGNLGYRASAKKAQICQKQVKYLGYLLKEGQ SEQ ID NO: 5: generic Shorter w/o c-term extension FLV:
RWLTKARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAYLSK
KLDTVASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQPLPDA
DLTWYT (D/G/N/A)GSS (F/I)IRNGERKAGAAVTTESEVIWAASLPPGTSAQRAELIALTQA
LKMAKGKKLTVYTDSRYAFATAHV (H/K)GEIYRRRG (L/W)LTS (E/K)GKEIKNKNEILAL
LEALFLPKRLSII (H/Y)CPGHQKGDSPQAKGNRLADDTAKKAATETQSSLTIL SEQ ID NO: 6: with longer c-term extension FLV: generic
RWLTKARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAYLSK
KLDTVASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQPLPDA
DLTWYT (D/G/N/A)GSS (F/I)IRNGERKAGAAVTTESEVIWAASLPPGTSAQRAELIALTQA
LKMAKGKKLTVYTDSRYAFATAHV (H/K)GEIYRRRG (L/W)LTS (E/K)GKEIKNKNEILAL
LEALFLPKRLSII (H/Y)CPGHQKGDSPQAKGNRLADDTAKKAATETQSSLTILPTELIEGPK
RPPWEY SEQ ID NO: 7: Shorter w/o c-term extension FLV: specific 522,
526, 632
RWLTKARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAYLSK
KLDTVASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQPLPDA
DLTWYTAGSS IIRNGERKAGAAVTTESEVIWAASLPPGTSAQRAELIALTQALKMAKGK
KLTVYTDSRYAFATAHVHGEIYRRRGLLTSEGKEIKNKNEILALLEALFLPKRLSII YCPG
HQKGDSPQAKGNRLADDTAKKAATETQSSLTIL SEQ ID NO: 8: with longer c-term extension FLV: 522, 601, 605
RWLTKARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAYLSK
KLDTVASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQPLPDA
DLTWYTGGSSFIRNGERKAGAAVTTESEVIWAASLPPGTSAQRAELIALTQALKMAKGK
KLTVYTDSRYAFATAHVHGEIYRRRGWLTSKGKEIKNKNEILALLEALFLPKRLSIIHCP
GHQKGDSPQAKGNRLADDTAKKAATETQSSLTILPTELIEGPKRPPWEY SEQ ID NO: 9: Shorter w/o c-term extension FLV: specific 522,
601, 605
RWLTKARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAYLSK
KLDTVASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQPLPDA
DLTWYTGGSSFIRNGERKAGAAVTTESEVIWAASLPPGTSAQRAELIALTQALKMAKGK
KLTVYTDSRYAFATAHVHGEIYRRRGWLTSKGKEIKNKNEILALLEALFLPKRLSIIHCP
GHQKGDSPQAKGNRLADDTAKKAATETQSSLTIL SEQ ID NO: 10: long N-term w/o c-term extension FLV: generic
YVDDLLLAAATRTECLEGTKALLETLGNKGYRASAKKAQICLQEVTYLGYSLKDGQRW -continued

| SEQUENCES |
|---|
| LTKARKEAILSIPVPKNPRQVREFLGTAGYCRLWIPGFAELAAPLYPLTRPGTLFQWGTE<br>QQLAFENIRKALLSSPALGLPDITKPFELFIDENSGFAKGVLVQKLGPWKRPVAYLSKKL<br>DTVASGWPPCLRMVAAIAILVKDAGKLTLGQPLTILTSHPVEALVRQPPNKWLSNARMT<br>HYQAMLLDAERVHFGPTVSLNPATLLPLPSGKPPRLSPDLAETMAQTDLTDQPLPDADL<br>TWYT (D/G/N/A)GSS (F/I)IRNGERKAGAAVTTESEVIWAASLPPGTSAQRAELIALTQALK<br>MAKGKKLTVYTDSRYAFATAHV (H/N)GEIYRRRG (L/W)LTS (E/K)GKEIKNKNEILALLE<br>ALFLPKRLSII (H/Y)CPGHQKGDSPQAKGNRLADDTAKKAATETQSSLTIL |
| SEQ ID NO: 11: long N-term w/o c-term extension FLV: specific<br>522, 601, 605<br>YVDDLLLAAATRTECLEGTKALLETLGNKGYRASAKKAQICLQEVTYLGYSLKDGQRW<br>LTKARKEAILSIPVPKNPRQVREFLGTAGYCRLWIPGFAELAAPLYPLTRPGTLFQWGTE<br>QQLAFENIRKALLSSPALGLPDITKPFELFIDENSGFAKGVLVQKLGPWKRPVAYLSKKL<br>DTVASGWPPCLRMVAAIAILVKDAGKLTLGQPLTILTSHPVEALVRQPPNKWLSNARMT<br>HYQAMLLDAERVHFGPTVSLNPATLLPLPSGKPPRLSPDLAETMAQTDLTDQPLPDADL<br>TWYTGGSSFIRNGERKAGAAVTTESEVIWAASLPPGTSAQRAELIALTQALKMAKGKKL<br>TVYTDSRYAFATAHVHGEIYRRRGWLTSKGKEIKNKNEILALLEALFLPKRLSIIHCPGH<br>QKGDSPQAKGNRLADDTAKKAATETQSSLTIL |
| SEQ ID NO: 12: long N-term w/o c-term extension FLV: specific<br>479, 592, 601<br>YVDDLLLAAATRTECLEGTKALLETLGNKGYRASAKKAQICLQEVTYLGYSLKDGQRW<br>LTKARKEAILSIPVPKNPRQVREFLGTAGYCRLWIPGFAELAAPLYPLTRPGTLFQWGTE<br>QQLAFENIRKALLSSPALGLPDITKPFELFIDENSGFAKGVLVQKLGPWKRPVAYLSKKL<br>DTVASGWPPCLRMVAAIAILVKDAGKLTLGQPLTILTSHPVEALVRQPPNKWLSNARMT<br>HYQAMLLDAERVHFGPTVSL[illegible]PATLLPLPSGKPPRLSPDLAETMAQTDLTDQPLPDADL<br>TWYTDGSSFIRNGERKAGAAVTTESEVIWAASLPPGTSAQRAELIALTQALKMAKGKKL<br>TVYTDSRYAFATAHV[illegible]GEIYRRRG[illegible]LTSEGKEIKNKNEILALLEALFLPKRLSIIHCPGH<br>QKGDSPQAKGNRLADDTAKKAATETQSSLTIL |
| SEQ ID NO: 13: long N-term w/o c-term extension FLV: specific<br>522, 601, 651<br>YVDDLLLAAATRTECLEGTKALLETLGNKGYRASAKKAQICLQEVTYLGYSLKDGQRW<br>LTKARKEAILSIPVPKNPRQVREFLGTAGYCRLWIPGFAELAAPLYPLTRPGTLFQWGTE<br>QQLAFENIRKALLSSPALGLPDITKPFELFIDENSGFAKGVLVQKLGPWKRPVAYLSKKL<br>DTVASGWPPCLRMVAAIAILVKDAGKLTLGQPLTILTSHPVEALVRQPPNKWLSNARMT<br>HYQAMLLDAERVHFGPTVSLNPATLLPLPSGKPPRLSPDLAETMAQTDLTDQPLPDADL<br>TWYT[illegible]GSSFIRNGERKAGAAVTTESEVIWAASLPPGTSAQRAELIALTQALKMAKGKKL<br>TVYTDSRYAFATAHVHGEIYRRRG[illegible]LTSEGKEIKNKNEILALLEALFLPKRLSIIHCPGH<br>QKGDSPQAKGNRLA[illegible]DTAKKAATETQSSLTIL |
| SEQ ID NO: 14: NF5PNAIY without leader or end sequences:<br>MTLNIEDEYRLHETSKEPDVSLGSTWLSDFPQAWAETGGMGLAVRQAPLIIPLKATSTPV<br>SIKQYPMSQEARLGIKPHIQRLLDQGILVPCQSPWNTPLLPVKKPGTNDYRPVQDLREVN<br>KRVEDIHPTVPNPYNLLSGPPPSHQWYTVLDLKDAFFCLRLHPTSQPLFAFEWRDPEMGI<br>SGQLTWTRLPQGFKNSPTLFNEALHRDLADFRIQHPDLILLQYVDDLLLAATSELDCQQ<br>GTRALLQTLGNLGYRASAKKAQICQKQVKYLGYLLKEGQRWLTKARKEAILSIPVPKNP<br>RQVREFLGTAGYCRLWIPGFAELAAPLYPLTRPGTLFQWGTEQQLAFENIRKALLSSPAL<br>GLPDITKPFELFIDENSGFAKGVLVQKLGPWKRPVAYLSKKLDTVASGWPPCLRMVAAI<br>AILVKDAGKLTLGQPLTILTSHPVEALVRQPPNKWLSNARMTHYQAMLLDAERVHFGP<br>TVSLNPATLLPLPSGKPPRLSPDLAETMAQTDLTDQPLPDADLTWYTAGSSIIRNGERKA<br>GAAVTTESEVIWAASLPPGTSAQRAELIALTQALKMAKGKKLTVYTDSRYAFATAHVH<br>GEIYRRRGLLTSEGKEIKNKNEILALLEALFLPKRLSIIYCPGHQKGDSPQAKGNRLADDT<br>AKKAATETQSSLTIL |
| SEQ ID NO: 15: MF4GC without leader or end sequences:<br>MTLNIEDEYRLHETSKEPDVSLGSTWLSDFPQAWAETGGMGLAVRQAPLIIPLKATSTPV<br>SIKQYPMSQEARLGIKPHIQRLLDQGILVPCQSPWNTPLLPVKKPGTNDYRPVQDLREVN<br>KRVEDIHPTVPNPYNLLSGKPPSHQWYTVLDLKDAFFCLRLHPTSQPLFAFEWRDPEMGI<br>SGQLTWTRLPQGFKNSPTLFNEALHRDLADFRIQHPDLILLQYVDDLLLAATSELDCQQ<br>GTRALLQTLGNLGYRASAKKAQICQKQVKYLGYLLKEGQRWLTKARKEAILSIPVPKNP<br>RQVREFLGTAGYCRLWIPGFAELAAPLYPLTRPGTLFQWGTEQQLAFENIRKALLSSPAL<br>GLPDITKPFELFIDENSGFAKGVLVQKLGPWKRPVAYLSKKLDTVASGWPPCLRMVAAI<br>AILVKDAGKLTLGQPLTILTSHPVEALVRQPPNKWLSNARMTHYQAMLLDAERVHFGP<br>TVSLNPATLLPLPSGKPPRLSPDLAETMAQTDLTDQPLPDADLTWYTGGSSFIRNGERKA<br>GAAVTTESEVIWAASLPPGTSAQRAELIALTQALKMAKGKKLTVYTDSRYAFATAHVH<br>GEIYRRRGWLTSKGKEIKNKNEILALLEALFLPKRLSIIHCPGHQKGDSPQAKGNRLADD<br>TAKKAATETQSSLTILPTELIEGPKRPPWEY |
| SEQ ID NO: 16: MF4G without leader or end sequences:<br>MTLNIEDEYRLHETSKEPDVSLGSTWLSDFPQAWAETGGMGLAVRQAPLIIPLKATSTPV<br>SIKQYPMSQEARLGIKPHIQRLLDQGILVPCQSPWNTPLLPVKKPGTNDYRPVQDLREVN<br>KRVEDIHPTVPNPYNLLSGPPPSHQWYTVLDLKDAFFCLRLHPTSQPLFAFEWRDPEMGI<br>SGQLTWTRLPQGFKNSPTLFNEALHRDLADFRIQHPDLILLQYVDDLLLAATSELDCQQ<br>GTRALLQTLGNLGYRASAKKAQICQKQVKYLGYLLKEGQRWLTKARKEAILSIPVPKNP<br>RQVREFLGTAGYCRLWIPGFAELAAPLYPLTRPGTLFQWGTEQQLAFENIRKALLSSPAL |

-continued

SEQUENCES

GLPDITKPFELFIDENSGFAKGVLVQKLGPWKRPVAYLSKKLDTVASGWPPCLRMVAAI
AILVKDAGKLTLGQPLTILTSHPVEALVRQPPNKWLSNARMTHYQAMLLDAERVHFGP
TVSLNPATLLPLPSGKPPRLSPDLAETMAQTDLTDQPLPDADLTWYTGGSSFIRNGERKA
GAAVTTESEVIWAASLPPGTSAQRAELIALTQALKMAKGKKLTVYTDSRYAFATAHVH
GEIYRRRGWLTSKGKEIKNKNEILALLEALFLPKRLSIIHCPGHQKGDSPQAKGNRLADD
TAKKAATETQSSLTIL

SEQ ID NO: 17: MF4(P)G without leader or end sequences:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQYVDDLLLAAATRTECLEG
TKALLETLGNKGYRASAKKAQICLQEVTYLGYSLKDGQRWLTKARKEAILSIPVPKNPR
QVREFLGTAGYCRLWIPGFAELAAPLYPLTRPGTLFQWGTEQQLAFENIRKALLSSPALG
LPDITKPFELFIDENSGFAKGVLVQKLGPWKRPVAYLSKKLDTVASGWPPCLRMVAAIA
ILVKDAGKLTLGQPLTILTSHPVEALVRQPPNKWLSNARMTHYQAMLLDAERVHFGPT
VSLNPATLLPLPSGKPPRLSPDLAETMAQTDLTDQPLPDADLTWYTGGSSFIRNGERKAG
AAVTTESEVIWAASLPPGTSAQRAELIALTQALKMAKGKKLTVYTDSRYAFATAHVHG
EIYRRRGWLTSKGKEIKNKNEILALLEALFLPKRLSIIHCPGHQKGDSPQAKGNRLADDT
AKKAATETQSSLTIL SEQ ID NO: 18: MF(P)4NDKW without leader or end sequences:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGLPPSHQWYTVLDLKDAFFCLRLHPTSQPLFAFEWRDPEMGI
SGQLTWTRLPQGFKNSPTLFNEALHRDLADFRIQHPDLILLQYVDDLLLAAATRTECLEG
TKALLETLGNKGYRASAKKAQICLQEVTYLGYSLKDGQRWLTKARKEAILSIPVPKNPR
QVREFLGTAGYCRLWIPGFAELAAPLYPLTRPGTLFQWGTEQQLAFENIRKALLSSPALG
LPDITKPFELFIDENSGFAKGVLVQKLGPWKRPVAYLSKKLDTVASGWPPCLRMVAAIA
ILVKDAGKLTLGQPLTILTSHPVEALVRQPPNKWLSNARMTHYQAMLLDAERVHFGPT
VSLDPATLLPLPSGKPPRLSPDLAETMAQTDLTDQPLPDADLTWYTDGSSFIRNGERKAG
AAVTTESEVIWAASLPPGTSAQRAELIALTQALKMAKGKKLTVYTDSRYAFATAHVKG
EIYRRRGWLTSEGKEIKNKNEILALLEALFLPKRLSIIHCPGHQKGDSPQAKGNRLADDT
AKKAATETQSSLTIL SEQ ID NO: 19: MF(P)4NGWN without leader or end sequences:
YVDDLLLAAATRTECLEGTKALLETLGNKGYRASAKKAQICLQEVTYLGYSLKDGQRW
LTKARKEAILSIPVPKNPRQVREFLGTAGYCRLWIPGFAELAAPLYPLTRPGTLFQWGTE
QQLAFENIRKALLSSPALGLPDITKPFELFIDENSGFAKGVLVQKLGPWKRPVAYLSKKL
DTVASGWPPCLRMVAAIAILVKDAGKLTLGQPLTILTSHPVEALVRQPPNKWLSNARMT
HYQAMLLDAERVHFGPTVSLNPATLLPLPSGKPPRLSPDLAETMAQTDLTDQPLPDADL
TWYTGGSSFIRNGERKAGAAVTTESEVIWAASLPPGTSAQRAELIALTQALKMAKGKKL
TVYTDSRYAFATAHVHGEIYRRRGWLTSEGKEIKNKNEILALLEALFLPKRLSIIHCPGH
QKGDSPQAKGNRLANDTAKKAATETQSSLTIL SEQ ID NO: 20: NF5PNAIY with leader and end sequences:
MGSSHHHHHHSSGLVPRGSHMTLNIEDEYRLHETSKEPDVSLGSTWLSDFPQAWAETG
GMGLAVRQAPLIIPLKATSTPVSIKQYPMSQEARLGIKPHIQRLLDQGILVPCQSPWNTPL
LPVKKPGTNDYRPVQDLREVNKRVEDIHPTVPNPYNLLSGPPPSHQWYTVLDLKDAFFC
LRLHPTSQPLFAFEWRDPEMGISGQLTWTRLPQGFKNSPTLFNEALHRDLADFRIQHPDL
ILLQYVDDLLLAATSELDCQQGTRALLQTLGNLGYRASAKKAQICQKQVKYLGYLLKE
GQRWLTKARKEAILSIPVPKNPRQVREFLGTAGYCRLWIPGFAELAAPLYPLTRPGTLFQ
WGTEQQLAFENIRKALLSSPALGLPDITKPFELFIDENSGFAKGVLVQKLGPWKRPVAYL
SKKLDTVASGWPPCLRMVAAIAILVKDAGKLTLGQPLTILTSHPVEALVRQPPNKWLSN
ARMTHYQAMLLDAERVHFGPTVSLNPATLLPLPSGKPPRLSPDLAETMAQTDLTDQPLP
DADLTWYTAGSSIIRNGERKAGAAVTTESEVIWAASLPPGTSAQRAELIALTQALKMAK
GKKLTVYTDSRYAFATAHVHGEIYRRRGLLTSEGKEIKNKNEILALLEALFLPKRLSIIYC
PGHQKGDSPQAKGNRLADDTAKKAATETQSSLTILAAA SEQ ID NO: 21: MF4GC with leader and end sequences:
MGSSHHHHHHSSGLVPRGSHMTLNIEDEYRLHETSKEPDVSLGSTWLSDFPQAWAETG
GMGLAVRQAPLIIPLKATSTPVSIKQYPMSQEARLGIKPHIQRLLDQGILVPCQSPWNTPL
LPVKKPGTNDYRPVQDLREVNKRVEDIHPTVPNPYNLLSGPPPSHQWYTVLDLKDAFFC
LRLHPTSQPLFAFEWRDPEMGISGQLTWTRLPQGFKNSPTLFNEALHRDLADFRIQHPDL
ILLQYVDDLLLAATSELDCQQGTRALLQTLGNLGYRASAKKAQICQKQVKYLGYLLKE
GQRWLTKARKEAILSIPVPKNPRQVREFLGTAGYCRLWIPGFAELAAPLYPLTRPGTLFQ
WGTEQQLAFENIRKALLSSPALGLPDITKPFELFIDENSGFAKGVLVQKLGPWKRPVAYL
SKKLDTVASGWPPCLRMVAAIAILVKDAGKLTLGQPLTILTSHPVEALVRQPPNKWLSN
ARMTHYQAMLLDAERVHFGPTVSLNPATLLPLPSGKPPRLSPDLAETMAQTDLTDQPLP
DADLTWYTGGSSFIRNGERKAGAAVTTESEVIWAASLPPGTSAQRAELIALTQALKMAK
GKKLTVYTDSRYAFATAHVHGEIYRRRGWLTSKGKEIKNKNEILALLEALFLPKRLSIIH
CPGHQKGDSPQAKGNRLADDTAKKAATETQSSLTILPTELIEGPKRPPWEYAAA SEQ ID NO: 22: MF4G with leader and end sequences:
MGSSHHHHHHSSGLVPRGSHMTLNIEDEYRLHETSKEPDVSLGSTWLSDFPQAWAETG
GMGLAVRQAPLIIPLKATSTPVSIKQYPMSQEARLGIKPHIQRLLDQGILVPCQSPWNTPL
LPVKKPGTNDYRPVQDLREVNKRVEDIHPTVPNPYNLLSGPPPSHQWYTVLDLKDAFFC -continued

SEQUENCES

LRLHPTSQPLFAFEWRDPEMGISGQLTWTRLPQGFKNSPTLFNEALHRDLADFRIQHPDL
ILLQYVDDLLLAATSELDCQQGTRALLQTLGNLGYRASAKKAQICQKQVKYLGYLLKE
GQRWLTKARKEAILSIPVPKNPRQVREFLGTAGYCRLWIPGFAELAAPLYPLTRPGTLFQ
WGTEQQLAFENIRKALLSSPALGLPDITKPFELFIDENSGFAKGVLVQKLGPWKRPVAYL
SKKLDTVASGWPPCLRMVAAIAILVKDAGKLTLGQPLTILTSHPVEALVRQPPNKWLSN
ARMTHYQAMLLDAERVHFGPTVSLNPATLLPLPSGKPPRLSPDLAETMAQTDLTDQPLP
DADLTWYTGGSSFIRNGERKAGAAVTTESEVIWAASLPPGTSAQRAELIALTQALKMAK
GKKLTVYTDSRYAFATAHVHGEIYRRRGWLTSKGKEIKNKNEILALLEALFLPKRLSIIH
CPGHQKGDSPQAKGNRLADDTAKKAATETQSSLTILAAA

SEQ ID NO: 23: MF(P)4G with leader and end sequences:
MGSSHHHHHHSSGLVPRGSHMTLNIEDEYRLHETSKEPDVSLGSTWLSDFPQAWAETG
GMGLAVRQAPLIIPLKATSTPVSIKQYPMSQEARLGIKPHIQRLLDQGILVPCQSPWNTPL
LPVKKPGTNDYRPVQDLREVNKRVEDIHPTVPNPYNLLSGGPPSHQWYTVLDLKDAFFC
LRLHPTSQPLFAFEWRDPEMGISGQLTWTRLPQGFKNSPTLFNEALHRDLADFRIQHPDL
ILLQYVDDLLLAAATRTECLEGTKALLETLGNKGYRASAKKAQICLQEVTYLGYSLKDG
QRWLTKARKEAILSIPVPKNPRQVREFLGTAGYCRLWIPGFAELAAPLYPLTRPGTLFQW
GTEQQLAFENIRKALLSSPALGLPDITKPFELFIDENSGFAKGVLVQKLGPWKRPVAYLS
KKLDTVASGWPPCLRMVAAIAILVKDAGKLTLGQPLTILTSHPVEALVRQPPNKWLSNA
RMTHYQAMLLDAERVHFGPTVSLNPATLLPLPSGKPPRLSPDLAETMAQTDLTDQPLPD
ADLTWYTGGSSFIRNGERKAGAAVTTESEVIWAASLPPGTSAQRAELIALTQALKMAKG
KKLTVYTDSRYAFATAHVHGEIYRRRGWLTSKGKEIKNKNEILALLEALFLPKRLSIIHC
PGHQKGDSPQAKGNRLADDTAKKAATETQSSLTILAAA SEQ ID NO: 24: MF(P)4NDKW with leader and end sequences:
MGSSHHHHHHSSGLVPRGSHMTLNIEDEYRLHETSKEPDVSLGSTWLSDFPQAWAETG
GMGLAVRQAPLIIPLKATSTPVSIKQYPMSQEARLGIKPHIQRLLDQGILVPCQSPWNTPL
LPVKKPGTNDYRPVQDLREVNKRVEDIHPTVPNPYNLLSGLPPSHQWYTVLDLKDAFFC
LRLHPTSQPLFAFEWRDPEMGISGQLTWTRLPQGFKNSPTLFNEALHRDLADFRIQHPDL
ILLQYVDDLLLAAATRTECLEGTKALLETLGNKGYRASAKKAQICLQEVTYLGYSLKDG
QRWLTKARKEAILSIPVPKNPRQVREFLGTAGYCRLWIPGFAELAAPLYPLTRPGTLFQW
GTEQQLAFENIRKALLSSPALGLPDITKPFELFIDENSGFAKGVLVQKLGPWKRPVAYLS
KKLDTVASGWPPCLRMVAAIAILVKDAGKLTLGQPLTILTSHPVEALVRQPPNKWLSNA
RMTHYQAMLLDAERVHFGPTVSLDPATLLPLPSGKPPRLSPDLAETMAQTDLTDQPLPD
ADLTWYTDGSSFIRNGERKAGAAVTTESEVIWAASLPPGTSAQRAELIALTQALKMAKG
KKLTVYTDSRYAFATAHVKGEIYRRRGWLTSEGKEIKNKNEILALLEALFLPKRLSIIHCP
GHQKGDSPQAKGNRLADDTAKKAATETQSSLTILAAA SEQ ID NO: 25: MF(P)4NGWN with leader and end sequences:
MGSSHHHHHHSSGLVPRGSHMTLNIEDEYRLHETSKEPDVSLGSTWLSDFPQAWAETG
GMGLAVRQAPLIIPLKATSTPVSIKQYPMSQEARLGIKPHIQRLLDQGILVPCQSPWNTPL
LPVKKPGTNDYRPVQDLREVNKRVEDIHPTVPNPYNLLSGLPPSHQWYTVLDLKDAFFC
LRLHPTSQPLFAFEWRDPEMGISGQLTWTRLPQGFKNSPTLFNEALHRDLADFRIQHPDL
ILLQYVDDLLLAAATRTECLEGTKALLETLGNKGYRASAKKAQICLQEVTYLGYSLKDG
QRWLTKARKEAILSIPVPKNPRQVREFLGTAGYCRLWIPGFAELAAPLYPLTRPGTLFQW
GTEQQLAFENIRKALLSSPALGLPDITKPFELFIDENSGFAKGVLVQKLGPWKRPVAYLS
KKLDTVASGWPPCLRMVAAIAILVKDAGKLTLGQPLTILTSHPVEALVRQPPNKWLSNA
RMTHYQAMLLDAERVHFGPTVSLNPATLLPLPSGKPPRLSPDLAETMAQTDLTDQPLPD
ADLTWYTGGSSFIRNGERKAGAAVTTESEVIWAASLPPGTSAQRAELIALTQALKMAKG
KKLTVYTDSRYAFATAHVHGEIYRRRGWLTSEGKEIKNKNEILALLEALFLPKRLSIIHCP
GHQKGDSPQAKGNRLANDTAKKAATETQSSLTILAAA SEQ ID NO: 26: 1/3 FLV N-terminus
MTLQLEEEYRLFEPESTQKQEMDIWLKNFPQAWAETGGMGMAHCQAPVLIQLKATATP
ISIRQYPMPHEAYQGIKPHIRRMLDQGILKPCQSPWNTPLLPVKKPGTKDYRPVQDLREV
NKRVEDIHPTVPNPYNLLSTLPPSHPWYTVLDLKDAFFCLRLHSESQLLFAFEWRDPEIG
LSGQLTWTRLPQGFKNSPTLFDEALHSDLADFRVRYPALVLLQYVDDLLLAAATRTECL
EGTKALLETLGNKGYRASAKKAQICLQEVTYLGYSLKDGQRW SEQ ID NO: 27 2/3 FLV N-terminus
MTLQLEEEYRLFEPESTQKQEMDIWLKNFPQAWAETGGMGMAHCQAPVLIQLKATATP
ISIRQYPMPHEAYQGIKPHIRRMLDQGILKPCQSPWNTPLLPVKKPGTKDYRPVQDLREV
NKRVEDIHPTVPNPYNLLSTLPPSHPWYTVLDLKDAFFCLRLHSESQLLFAFEWRDPEIG
LSGQLTWTRLPQGFKNSPTLFDEALHSDLADFRVRYPALVLLQYVDDLLLAAATRTECL
EGTKALLETLGNKGYRASAKKAQICLQEVTYLGYSLKDGQRWLTKARKEAILSIPVPKN
PRQVREFLGTAGYCRLWIPGFAELAAPLYPLTRPGTLFQWGTEQQLAFENIRKALLSSPA
LGLPDITKPFELFIDENSGFAKGVLVQKLGPWKRPVAYLSKKLDTVASGWPPCLRMVAA
IAILVKDAGKLTLGQPLTILTSHPVEALVRQPPNKWLSNARMTHYQAMLLDAERVHFGP
TVSLNPATLLPLPSGKPPRLSPD SEQ ID NO: 28 2/3 MLV C-terminus
LTEARKETVMGQPTPKTPRQLREFLGTAGFCRLWIPGFAEMAAPLYPLTKTGTLFNWGP
DQQKAYQEIKQALLTAPALGLPDLTKPFELFVDEKQGYAKGVLTQKLGPWRRPVAYLS
KKLDPVAAGWPPCLRMVAAIAVLTKDAGKLTMGQPLVILAPHAVEALVKQPPDRWLS
NARMTHYQALLLDTDRVQFGPVVALNPATLLPLPEEGLQHDCLDILAEAHGTRSDLTD
QPLPDADHTWYTDGSSFLQEGQRKAGAAVTTETEVIWARALPAGTSAQRAELIALTQA -continued

| SEQUENCES |
| --- |

LKMAEGKKLNVYTDSRYAFATAHIHGEIYRRRGLLTSEGKEIKNKDEILALLKALFLPKR
LSIIHCPGHQKGNSAEARGNRMADQAAREVATRETPGTSTLL

SEQ ID NO: 29 $^{1}/_{3}$ MLV C-terminus
ILAEAHGTRSDLTDQPLPDADHTWYTDGSSFLQEGQRKAGAAVTTETEVIWARALPAG
TSAQRAELIALTQALKMAEGKKLNVYTDSRYAFATAHIHGEIYRRRGLLTSEGKEIKNK
DEILALLKALFLPKRLSIIHCPGHQKGNSAEARGNRMADQAAREVATRETPGTSTLL SEQ ID NO: 30 FM1 ($^{1}/_{3}$ FLV-$^{2}/_{3}$ MLV RT)
MTLQLEEEYRLFEPESTQKQEMDIWLKNFPQAWAETGGMGMAHCQAPVLIQLKATATP
ISIRQYPMPHEAYQGIKPHIRRMLDQGILKPCQSPWNTPLLPVKKPGTKDYRPVQDLREV
NKRVEDIHPTVPNPYNLLSTLPPSHPWYTVLDLKDAFFCLRLHSESQLLFAFEWRDPEIG
LSGQLTWTRLPQGFKNSPTLFDEALHSDLADFRVRYPALVLLQYVDDLLLAAATRTECL
EGTKALLETLGNKGYRASAKKAQICLQEVTYLGYSLKDGQRWLTEARKETVMGQPTPK
TPRQLREFLGTAGFCRLWIPGFAEMAAPLYPLTKTGTLFNWGPDQQKAYQEIKQALLTA
PALGLPDLTKPFELFVDEKQGYAKGVLTQKLGPWRRPVAYLSKKLDPVAAGWPPCLR
MVAAIAVLTKDAGKLTMGQPLVILAPHAVEALVKQPPDRWLSNARMTHYQALLLDTD
RVQFGPVVALNPATLLPLPEEGLQHDCLDILAEAHGTRSDLTDQPLPDADHTWYTDGSS
FLQEGQRKAGAAVTTETEVIWARALPAGTSAQRAELIALTQALKMAEGKKLNVYTDSR
YAFATAHIHGEIYRRRGLLTSEGKEIKNKDEILALLKALFLPKRLSIIHCPGHQKGNSAEA
RGNRMADQAAREVATRETPGTSTLL SEQ ID NO: 31 FM2 ($^{2}/_{3}$ FLV-$^{1}/_{3}$ MLV RT)
MTLQLEEEYRLFEPESTQKQEMDIWLKNFPQAWAETGGMGMAHCQAPVLIQLKATATP
ISIRQYPMPHEAYQGIKPHIRRMLDQGILKPCQSPWNTPLLPVKKPGTKDYRPVQDLREV
NKRVEDIHPTVPNPYNLLSTLPPSHPWYTVLDLKDAFFCLRLHSESQLLFAFEWRDPEIG
LSGQLTWTRLPQGFKNSPTLFDEALHSDLADFRVRYPALVLLQYVDDLLLAAATRTECL
EGTKALLETLGNKGYRASAKKAQICLQEVTYLGYSLKDGQRWLTKARKEAILSIPVPKN
PRQVREFLGTAGYCRLWIPGFAELAAPLYPLTRPGTLFQWGTEQQLAFENIRKALLSSPA
LGLPDITKPFELFIDENSGFAKGVLVQKLGPWKRPVAYLSKKLDTVASGWPPCLRMVAA
IAILVKDAGKLTLGQPLTILTSHPVEALVRQPPNKWLSNARMTHYQAMLLDAERVHFGP
TVSLNPATLLPLPSGKPPRLSPDILAEAHGTRSDLTDQPLPDADHTWYTDGSSFLQEGQR
KAGAAVTTETEVIWARALPAGTSAQRAELIALTQALKMAEGKKLNVYTDSRYAFATAH
IHGEIYRRRGLLTSEGKEIKNKDEILALLKALFLPKRLSIIHCPGHQKGNSAEARGNRMAD
QAAREVATRETPGTSTLL SEQ ID NO: 32 Wild type MLV RT sequence
TLNIEDEHRLHETSKEPDVSLGSTWLSDFPQAWAETGGMGLAVRQAPLIIPLKATSTPVSI
KQYPMSQEARLGIKPHIQRLLDQGILVPCQSPWNTPLLPVKKPGTNDYRPVQDLREVNK
RVEDIHPTVPNPYNLLSGLPPSHQWYTVLDLKDAFFCLRLHPTSQPLFAFEWRDPEMGIS
GQLTWTRLPQGFKNSPTLFDEALHRDLADFRIQHPDLILLQYVDDLLLAATSELDCQQG
TRALLQTLGNLGYRASAKKAQICQKQVKYLGYLLKEGQRWLTEARKETVMGQPTPKT
PRQLREFLGTAGFCRLWIPGFAEMAAPLYPLTKTGTLFNWGPDQQKAYQEIKQALLTAP
ALGLPDLTKPFELFVDEKQGYAKGVLTQKLGPWRRPVAYLSKKLDPVAAGWPPCLRM
VAAIAVLTKDAGKLTMGQPLVILAPHAVEALVKQPPDRWLSNARMTHYQALLLDTDR
VQFGPVVALNPATLLPLPEEGLQHNCLDILAEAHGTRPDLTDQPLPDADHTWYTDGSSL
LQEGQRKAGAAVTTETEVIWAKALPAGTSAQRAELIALTQALKMAEGKKLNVYTDSRY
AFATAHIHGEIYRRRGLLTSEGKEIKNKDEILALLKALFLPKRLSIIHCPGHQKGHSAEAR
GNRMADQAARKAAITETPDTSTLL SEQ ID NO: 33 Wild type FLV RT sequence
TLQLEEEYRLFEPESTQKQEMDIWLKNFPQAWAETGGMGMAHCQAPVLIQLKATATPIS
IRQYPMPHEAYQGIKPHIRRMLDQGILKPCQSPWNTPLLPVKKPGTKDYRPVQDLREVN
KRVEDIHPTVPNPYNLLSTLPPSHPWYTVLDLKDAFFCLRLHSESQLLFAFEWRDPEIGLS
GQLTWTRLPQGFKNSPTLFDEALHSDLADFRVRYPALVLLQYVDDLLLAATRTECLEG
TKALLETLGNKGYRASAKKAQICLQEVTYLGYSLKDGQRWLTKARKEAILSIPVPKNPR
QVREFLGTAGYCRLWIPGFAELAAPLYPLTRPGTLFQWGTEQQLAFENIRKALLSSPALG
LPDITKPFELFIDENSGFAKGVLVQKLGPWKRPVAYLSKKLDTVASGWPPCLRMVAAIA
ILVKDAGKLTLGQPLTILTSHPVEALVRQPPNKWLSNARMTHYQAMLLDAERVHFGPT
VSLNPATLLPLPSGKPPRLSPDLAETMAQTDLTDQPLPDADLTWYTDGSSFIRNGERKAG
AAVTTESEVIWAASLPPGTSAQRAELIALTQALKMAKGKKLTVYTDSRYAFATAHVHG
EIYRRRGLLTSEGKEIKNKNEILALLEALFLPKRLSIIHCPGHQKGDSPQAKGNRLADDTA
KKAATETQSSLTIL SEQ ID NO: 34: NF5PNAIYC without leader or end sequences:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQYVDDLLLAATSELDCQQ
GTRALLQTLGNLGYRASAKKAQICQKQVKYLGYLLKEGQRWLTKARKEAILSIPVPKNP
RQVREFLGTAGYCRLWIPGFAELAAPLYPLTRPGTLFQWGTEQQLAFENIRKALLSSPAL
GLPDITKPFELFIDENSGFAKGVLVQKLGPWKRPVAYLSKKLDTVASGWPPCLRMVAAI
AILVKDAGKLTLGQPLTILTSHPVEALVRQPPNKWLSNARMTHYQAMLLDAERVHFGP
TVSLNPATLLPLPSGKPPRLSPDLAETMAQTDLTDQPLPDADLTWYTAGSSIIRNGERKA
GAAVTTESEVIWAASLPPGTSAQRAELIALTQALKMAKGKKLTVYTDSRYAFATAHVH
GEIYRRRGLLTSEGKEIKNKNEILALLEALFLPKRLSIIYCPGHQKGDSPQAKGNRLADDT
AKKAATETQSSLTILPTELIEGPKRPPWEY -continued

| SEQUENCES |
| --- |

SEQ ID NO: 35: MF4(P)GC without leader or end sequences:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQYVDDLLLAAATRTECLEG
TKALLETLGNKGYRASAKKAQICLQEVTYLGYSLKDGQRWLTKARKEAILSIPVPKNPR
QVREFLGTAGYCRLWIPGFAELAAPLYPLTRPGTLFQWGTEQQLAFENIRKALLSSPALG
LPDITKPFELFIDENSGFAKGVLVQKLGPWKRPVAYLSKKLDTVASGWPPCLRMVAAIA
ILVKDAGKLTLGQPLTILTSHPVEALVRQPPNKWLSNARMTHYQAMLLDAERVHFGPT
VSLNPATLLPLPSGKPPRLSPDLAETMAQTDLTDQPLPDADLTWYTGGSSFIRNGERKAG
AAVTTESEVIWAASLPPGTSAQRAELIALTQALKMAKGKKLTVYTDSRYAFATAHVHG
EIYRRRGWLTSKGKEIKNKNEILALLEALFLPKRLSIIHCPGHQKGDSPQAKGNRLADDT
AKKAATETQSSLTILPTELIEGPKRPPWEY SEQ ID NO: 36: NF5PNAIYC MLVRT portion:
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQYVDDLLLAATSELDCQQ
GTRALLQTLGNLGYRASAKKAQICQKQVKYLGYLLKEGQ SEQ ID NO: 37: NF5PNAIYC FLVRT portion:
RWLTKARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAYLSK
KLDTVASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQPLPDA
DLTWYTGGSSFIRNGERKAGAAVTTESEVIWAASLPPGTSAQRAELIALTQALKMAKGK
KLTVYTDSRYAFATAHVHGEIYRRRGLLTSEGKEIKNKNEILALLEALFLPKRLSIIHCPG
HQKGDSPQAKGNRLADDTAKKAATETQSSLTILPTELIEGPKRPPWEY SEQ ID NO: 38: MF4(P)GC MLVRT portion
MTLNIEDEYRLHETSKEPDVSLGSTWLSDFPQAWAETGGMGLAVRQAPLIIPLKATSTPV
SIKQYPMSQEARLGIKPHIQRLLDQGILVPCQSPWNTPLLPVKKPGTNDYRPVQDLREVN
KRVEDIHPTVPNPYNLLSGPPPSHQWYTVLDLKDAFFCLRLHPTSQPLFAFEWRDPEMGI
SGQLTWTRLPQGFKNSPTLFNEALHRDLADFRIQHPDLILLQ SEQ ID NO: 39: MF4(P)GC FLVRT portion
YVDDLLLAAATRTECLEGTKALLETLGNKGYRASAKKAQICLQEVTYLGYSLKDGQRW
LTKARKEAILSIPVPKNPRQVREFLGTAGYCRLWIPGFAELAAPLYPLTRPGTLFQWGTE
QQLAFENIRKALLSSPALGLPDITKPFELFIDENSGFAKGVLVQKLGPWKRPVAYLSKKL
DTVASGWPPCLRMVAAIAILVKDAGKLTLGQPLTILTSHPVEALVRQPPNKWLSNARMT
HYQAMLLDAERVHFGPTVSLNPATLLPLPSGKPPRLSPDLAETMAQTDLTDQPLPDADL
TWYTGGSSFIRNGERKAGAAVTTESEVIWAASLPPGTSAQRAELIALTQALKMAKGKKL
TVYTDSRYAFATAHVHGEIYRRRGWLTSKGKEIKNKNEILALLEALFLPKRLSIIHCPGH
QKGDSPQAKGNRLADDTAKKAATETQSSLTILPTELIEGPKRPPWEY SEQ ID NO: 40: NF5PNAIYC with leader and end sequences
MGSSHHHHHHSSGLVPRGSH*MTLNIEDEYRLHETSKEPDVSLGSTWLSDFPQAWAETGGM*
*GLAVRQAPLIIPLKATSTPVSIKQYPMSQEARLGIKPHIQRLLDQGILVPCQSPWNTPLLPVKKP*
*GTNDYRPVQDLREVNKRVEDIHPTVPNPYNLLSGPPPSHQWYTVLDLKDAFFCLRLHPTSQP*
*LFAFEWRDPEMGISGQLTWTRLPQGFKNSPTLFNEALHRDLADFRIQHPDLILLQ*YVDDLLL
AATSELDCQQGTRALLQTLGNLGYRASAKKAQICQKQVKYLGYLLKEGQRWLTKARKEAI
LSIPVPKNPRQVREFLGTAGYCRLWIPGFAELAAPLYPLTRPGTLFQWGTEQQLAF
ENIRKALLSSPALGLPDITKPFELFIDENSGFAKGVLVQKLGPWKRPVAYLSKKLDT
VASGWPPCLRMVAAIAILVKDAGKLTLGQPLTILTSHPVEALVRQPPNKWLSNAR
MTHYQAMLLDAERVHFGPTVSLNPATLLPLPSGKPPRLSPDLAETMAQTDLTDQP
LPDADLTWYTGGSSFIRNGERKAGAAVTTESEVIWAASLPPGTSAQRAELIALTQAL
KMAKGKKLTVYTDSRYAFATAHVHGEIYRRRGLLTSEGKEIKNKNEILALLEALFL
PKRLSIIHCPGHQKGDSPQAKGNRLADDTAKKAATETQSSLTILPTELIEGPKRPPW
EYAAA SEQ ID NO: 41: MF4(P)GC with leader and end sequences
MGSSHHHHHHSSGLVPRGSH*MTLNIEDEYRLHETSKEPDVSLGSTWLSDFPQAWAETGGM*
*GLAVRQAPLIIPLKATSTPVSIKQYPMSQEARLGIKPHIQRLLDQGILVPCQSPWNTPLLPVKKP*
*GTNDYRPVQDLREVNKRVEDIHPTVPNPYNLLSGPPPSHQWYTVLDLKDAFFCLRLHPTSQP*
*LFAFEWRDPEMGISGQLTWTRLPQGFKNSPTLFNEALHRDLADFRIQHPDLILLQ*YVDDLL
LAAATRTECLEGTKALLETLGNKGYRASAKKAQICLQEVTYLGYSLKDGQRWLT
KARKEAILSIPVPKNPRQVREFLGTAGYCRLWIPGFAELAAPLYPLTRPGTLFQWG
TEQQLAFENIRKALLSSPALGLPDITKPFELFIDENSGFAKGVLVQKLGPWKRPVAY
LSKKLDTVASGWPPCLRMVAAIAILVKDAGKLTLGQPLTILTSHPVEALVRQPPNK
WLSNARMTHYQAMLLDAERVHFGPTVSLNPATLLPLPSGKPPRLSPDLAETMAQT
DLTDQPLPDADLTWYTGGSSFIRNGERKAGAAVTTESEVIWAASLPPGTSAQRAELI

-continued

| SEQUENCES |
| --- |
| **ALTQALKMAKGKKLTVYTDSRYAFATAHVHGEIYRRRG[illegible]LTS[illegible]GKEIKNKNEILA LLEALFLPKRLSIIHCPGHQKGDSPQAKGNRLADDTAKKAATETQSSLTILPTELIE GPKRPPWEY**AAA |

SEQUENCE LISTING

```
Sequence total quantity: 42
SEQ ID NO: 1           moltype = AA  length = 222
FEATURE                Location/Qualifiers
REGION                 1..222
                       note = Synthetic construct
VARIANT                140
                       note = MISC_FEATURE - Xaa = Leu or Pro
VARIANT                201
                       note = MISC_FEATURE - Xaa = Asp or Asn
source                 1..222
                       mol_type = protein
                       organism = synthetic construct
SEQUENCE: 1
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGX PPSHQWYTVL DLKDAFFCLR LHPTSQPLFA FEWRDPEMGI  180
SGQLTWTRLP QGFKNSPTLF XEALHRDLAD FRIQHPDLIL LQ                   222

SEQ ID NO: 2           moltype = AA  length = 278
FEATURE                Location/Qualifiers
REGION                 1..278
                       note = Synthetic construct
VARIANT                140
                       note = MISC_FEATURE - Xaa = Leu or Pro
VARIANT                201
                       note = MISC_FEATURE - Xaa = Asp or Asn
source                 1..278
                       mol_type = protein
                       organism = synthetic construct
SEQUENCE: 2
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGX PPSHQWYTVL DLKDAFFCLR LHPTSQPLFA FEWRDPEMGI  180
SGQLTWTRLP QGFKNSPTLF XEALHRDLAD FRIQHPDLIL LQYVDDLLLA ATSELDCQQG  240
TRALLQTLGN LGYRASAKKA QICQKQVKYL GYLLKEGQ                         278

SEQ ID NO: 3           moltype = AA  length = 222
FEATURE                Location/Qualifiers
REGION                 1..222
                       note = Synthetic construct
source                 1..222
                       mol_type = protein
                       organism = synthetic construct
SEQUENCE: 3
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQ                   222

SEQ ID NO: 4           moltype = AA  length = 278
FEATURE                Location/Qualifiers
REGION                 1..278
                       note = Synthetic construct
source                 1..278
                       mol_type = protein
                       organism = synthetic construct
SEQUENCE: 4
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA ATSELDCQQG  240
TRALLQTLGN LGYRASAKKA QICQKQVKYL GYLLKEGQ                         278

SEQ ID NO: 5           moltype = AA  length = 391
FEATURE                Location/Qualifiers
REGION                 1..391
                       note = Synthetic construct
```

-continued

```
VARIANT                245
                       note = MISC_FEATURE - Xaa = Asp, Gly, Asn, or Ala
VARIANT                249
                       note = MISC_FEATURE - Xaa = Phe or Ile
VARIANT                315
                       note = MISC_FEATURE - Xaa = His or Lys
VARIANT                324
                       note = MISC_FEATURE - Xaa = Leu or Trp
VARIANT                328
                       note = MISC_FEATURE - Xaa = Glu or Lys
VARIANT                355
                       note = MISC_FEATURE - Xaa = His or Tyr
source                 1..391
                       mol_type = protein
                       organism = synthetic construct
SEQUENCE: 5
RWLTKARKEA ILSIPVPKNP RQVREFLGTA GYCRLWIPGF AELAAPLYPL TRPGTLFQWG  60
TEQQLAFENI RKALLSSPAL GLPDITKPFE LFIDENSGFA KGVLVQKLGP WKRPVAYLSK  120
KLDTVASGWP PCLRMVAAIA ILVKDAGKLT LGQPLTILTS HPVEALVRQP PNKWLSNARM  180
THYQAMLLDA ERVHFGPTVS LNPATLLPLP SGKPPRLSPD LAETMAQTDL TDQPLPDADL  240
TWYTXGSSXI RNGERKAGAA VTTESEVIWA ASLPPGTSAQ RAELIALTQA LKMAKGKKLT  300
VYTDSRYAFA TAHVXGEIYR RRGXLTSXGK EIKNKNEILA LLEALFLPKR LSIIXCPGHQ  360
KGDSPQAKGN RLADDTAKKA ATETQSSLTI L                                391

SEQ ID NO: 6           moltype = AA  length = 406
FEATURE                Location/Qualifiers
REGION                 1..406
                       note = Synthetic construct
VARIANT                245
                       note = MISC_FEATURE - Xaa = Asp, Gly, Asn, or Ala
VARIANT                249
                       note = MISC_FEATURE - Xaa = Phe or Ile
VARIANT                315
                       note = MISC_FEATURE - Xaa = His or Lys
VARIANT                324
                       note = MISC_FEATURE - Xaa = Leu or Trp
VARIANT                328
                       note = MISC_FEATURE - Xaa = Glu or Lys
VARIANT                355
                       note = MISC_FEATURE - Xaa = His or Tyr
source                 1..406
                       mol_type = protein
                       organism = synthetic construct
SEQUENCE: 6
RWLTKARKEA ILSIPVPKNP RQVREFLGTA GYCRLWIPGF AELAAPLYPL TRPGTLFQWG  60
TEQQLAFENI RKALLSSPAL GLPDITKPFE LFIDENSGFA KGVLVQKLGP WKRPVAYLSK  120
KLDTVASGWP PCLRMVAAIA ILVKDAGKLT LGQPLTILTS HPVEALVRQP PNKWLSNARM  180
THYQAMLLDA ERVHFGPTVS LNPATLLPLP SGKPPRLSPD LAETMAQTDL TDQPLPDADL  240
TWYTXGSSXI RNGERKAGAA VTTESEVIWA ASLPPGTSAQ RAELIALTQA LKMAKGKKLT  300
VYTDSRYAFA TAHVXGEIYR RRGXLTSXGK EIKNKNEILA LLEALFLPKR LSIIXCPGHQ  360
KGDSPQAKGN RLADDTAKKA ATETQSSLTI LPTELIEGPK RPPWEY                406

SEQ ID NO: 7           moltype = AA  length = 391
FEATURE                Location/Qualifiers
REGION                 1..391
                       note = Synthetic construct
source                 1..391
                       mol_type = protein
                       organism = synthetic construct
SEQUENCE: 7
RWLTKARKEA ILSIPVPKNP RQVREFLGTA GYCRLWIPGF AELAAPLYPL TRPGTLFQWG  60
TEQQLAFENI RKALLSSPAL GLPDITKPFE LFIDENSGFA KGVLVQKLGP WKRPVAYLSK  120
KLDTVASGWP PCLRMVAAIA ILVKDAGKLT LGQPLTILTS HPVEALVRQP PNKWLSNARM  180
THYQAMLLDA ERVHFGPTVS LNPATLLPLP SGKPPRLSPD LAETMAQTDL TDQPLPDADL  240
TWYTAGSSII RNGERKAGAA VTTESEVIWA ASLPPGTSAQ RAELIALTQA LKMAKGKKLT  300
VYTDSRYAFA TAHVHGEIYR RRGLLTSEGK EIKNKNEILA LLEALFLPKR LSIIYCPGHQ  360
KGDSPQAKGN RLADDTAKKA ATETQSSLTI L                                391

SEQ ID NO: 8           moltype = AA  length = 406
FEATURE                Location/Qualifiers
REGION                 1..406
                       note = Synthetic construct
source                 1..406
                       mol_type = protein
                       organism = synthetic construct
SEQUENCE: 8
RWLTKARKEA ILSIPVPKNP RQVREFLGTA GYCRLWIPGF AELAAPLYPL TRPGTLFQWG  60
TEQQLAFENI RKALLSSPAL GLPDITKPFE LFIDENSGFA KGVLVQKLGP WKRPVAYLSK  120
KLDTVASGWP PCLRMVAAIA ILVKDAGKLT LGQPLTILTS HPVEALVRQP PNKWLSNARM  180
```

-continued

THYQAMLLDA ERVHFGPTVS LNPATLLPLP SGKPPRLSPD LAETMAQTDL TDQPLPDADL 240
TWYTGGSSFI RNGERKAGAA VTTESEVIWA ASLPPGTSAQ RAELIALTQA LKMAKGKKLT 300
VYTDSRYAFA TAHVHGEIYR RRGWLTSKGK EIKNKNEILA LLEALFLPKR LSIIHCPGHQ 360
KGDSPQAKGN RLADDTAKKA ATETQSSLTI LPTELIEGPK RPPWEY 406

SEQ ID NO: 9 moltype = AA length = 391
FEATURE Location/Qualifiers
REGION 1..391
note = Synthetic construct
source 1..391
mol_type = protein
organism = synthetic construct
SEQUENCE: 9
RWLTKARKEA ILSIPVPKNP RQVREFLGTA GYCRLWIPGF AELAAPLYPL TRPGTLFQWG 60
TEQQLAFENI RKALLSSPAL GLPDITKPFE LFIDENSGFA KGVLVQKLGP WKRPVAYLSK 120
KLDTVASGWP PCLRMVAAIA ILVKDAGKLT LGQPLTILTS HPVEALVRQP PNKWLSNARM 180
THYQAMLLDA ERVHFGPTVS LNPATLLPLP SGKPPRLSPD LAETMAQTDL TDQPLPDADL 240
TWYTGGSSFI RNGERKAGAA VTTESEVIWA ASLPPGTSAQ RAELIALTQA LKMAKGKKLT 300
VYTDSRYAFA TAHVHGEIYR RRGWLTSKGK EIKNKNEILA LLEALFLPKR LSIIHCPGHQ 360
KGDSPQAKGN RLADDTAKKA ATETQSSLTI L 391

SEQ ID NO: 10 moltype = AA length = 447
FEATURE Location/Qualifiers
REGION 1..447
note = Synthetic construct
VARIANT 301
note = MISC_FEATURE - Xaa = Asp, Gly, Asn, or Ala
VARIANT 305
note = MISC_FEATURE - Xaa = Phe or Ile
VARIANT 371
note = MISC_FEATURE - Xaa = His or Lys
VARIANT 380
note = MISC_FEATURE - Xaa = Leu or Trp
VARIANT 384
note = MISC_FEATURE - Xaa = Glu or Lys
VARIANT 411
note = MISC_FEATURE - Xaa = His or Tyr
source 1..447
mol_type = protein
organism = synthetic construct
SEQUENCE: 10
YVDDLLLAAA TRTECLEGTK ALLETLGNKG YRASAKKAQI CLQEVTYLGY SLKDGQRWLT 60
KARKEAILSI PVPKNPRQVR EFLGTAGYCR LWIPGFAELA APLYPLTRPG TLFQWGTEQQ 120
LAFENIRKAL LSSPALGLPD ITKPFELFID ENSGFAKGVL VQKLGPWKRP VAYLSKKLDT 180
VASGWPPCLR MVAAIAILVK DAGKLTLGQP LTILTSHPVE ALVRQPPNKW LSNARMTHYQ 240
AMLLDAERVH FGPTVSLNPA TLLPLPSGKP PRLSPDLAET MAQTDLTDQP LPDADLTWYT 300
XGSSXIRNGE RKAGAAVTTE SEVIWAASLP PGTSAQRAEL IALTQALKMA KGKKLTVYTD 360
SRYAFATAHV XGEIYRRRGX LTSXGKEIKN KNEILALLEA LFLPKRLSII XCPGHQKGDS 420
PQAKGNRLAD DTAKKAATET QSSLTIL 447

SEQ ID NO: 11 moltype = AA length = 447
FEATURE Location/Qualifiers
REGION 1..447
note = Synthetic construct
source 1..447
mol_type = protein
organism = synthetic construct
SEQUENCE: 11
YVDDLLLAAA TRTECLEGTK ALLETLGNKG YRASAKKAQI CLQEVTYLGY SLKDGQRWLT 60
KARKEAILSI PVPKNPRQVR EFLGTAGYCR LWIPGFAELA APLYPLTRPG TLFQWGTEQQ 120
LAFENIRKAL LSSPALGLPD ITKPFELFID ENSGFAKGVL VQKLGPWKRP VAYLSKKLDT 180
VASGWPPCLR MVAAIAILVK DAGKLTLGQP LTILTSHPVE ALVRQPPNKW LSNARMTHYQ 240
AMLLDAERVH FGPTVSLNPA TLLPLPSGKP PRLSPDLAET MAQTDLTDQP LPDADLTWYT 300
GGSSFIRNGE RKAGAAVTTE SEVIWAASLP PGTSAQRAEL IALTQALKMA KGKKLTVYTD 360
SRYAFATAHV HGEIYRRRGW LTSKGKEIKN KNEILALLEA LFLPKRLSII HCPGHQKGDS 420
PQAKGNRLAD DTAKKAATET QSSLTIL 447

SEQ ID NO: 12 moltype = AA length = 447
FEATURE Location/Qualifiers
REGION 1..447
note = Synthetic construct
source 1..447
mol_type = protein
organism = synthetic construct
SEQUENCE: 12
YVDDLLLAAA TRTECLEGTK ALLETLGNKG YRASAKKAQI CLQEVTYLGY SLKDGQRWLT 60
KARKEAILSI PVPKNPRQVR EFLGTAGYCR LWIPGFAELA APLYPLTRPG TLFQWGTEQQ 120
LAFENIRKAL LSSPALGLPD ITKPFELFID ENSGFAKGVL VQKLGPWKRP VAYLSKKLDT 180
VASGWPPCLR MVAAIAILVK DAGKLTLGQP LTILTSHPVE ALVRQPPNKW LSNARMTHYQ 240

-continued

```
AMLLDAERVH FGPTVSLDPA TLLPLPSGKP PRLSPDLAET MAQTDLTDQP LPDADLTWYT  300
DGSSFIRNGE RKAGAAVTTE SEVIWAASLP PGTSAQRAEL IALTQALKMA KGKKLTVYTD  360
SRYAFATAHV KGEIYRRRGW LTSEGKEIKN KNEILALLEA LFLPKRLSII HCPGHQKGDS  420
PQAKGNRLAD DTAKKAATET QSSLTIL                                      447

SEQ ID NO: 13           moltype = AA  length = 447
FEATURE                 Location/Qualifiers
REGION                  1..447
                        note = Synthetic construct
source                  1..447
                        mol_type = protein
                        organism = synthetic construct
SEQUENCE: 13
YVDDLLLAAA TRTECLEGTK ALLETLGNKG YRASAKKAQI CLQEVTYLGY SLKDGQRWLT  60
KARKEAILSI PVPKNPRQVR EFLGTAGYCR LWIPGFAELA APLYPLTRPG TLFQWGTEQQ  120
LAFENIRKAL LSSPALGLPD ITKPFELFID ENSGFAKGVL VQKLGPWKRP VAYLSKKLDT  180
VASGWPPCLR MVAAIAILVK DAGKLTLGQP LTILTSHPVE ALVRQPPNKW LSNARMTHYQ  240
AMLLDAERVH FGPTVSLNPA TLLPLPSGKP PRLSPDLAET MAQTDLTDQP LPDADLTWYT  300
GGSSFIRNGE RKAGAAVTTE SEVIWAASLP PGTSAQRAEL IALTQALKMA KGKKLTVYTD  360
SRYAFATAHV HGEIYRRRGW LTSEGKEIKN KNEILALLEA LFLPKRLSII HCPGHQKGDS  420
PQAKGNRLAN DTAKKAATET QSSLTIL                                      447

SEQ ID NO: 14           moltype = AA  length = 669
FEATURE                 Location/Qualifiers
REGION                  1..669
                        note = Synthetic construct
source                  1..669
                        mol_type = protein
                        organism = synthetic construct
SEQUENCE: 14
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA ATSELDCQQG  240
TRALLQTLGN LGYRASAKKA QICQKQVKYL GYLLKEGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
VKDAGKLTLG QPLTILTSHP VEALVRQPPN KWLSNARMTH YQAMLLDAER VHFGPTVSLN  480
PATLLPLPSG KPPRLSPDLA ETMAQTDLTD QPLPDADLTW YTAGSSIIRN GERKAGAAVT  540
TESEVIWAAS LPPGTSAQRA ELIALTQALK MAKGKKLTVY TDSRYAFATA HVHGEIYRRR  600
GLLTSEGKEI KNKNEILALL EALFLPKRLS IIYCPGHQKG DSPQAKGNRL ADDTAKKAAT  660
ETQSSLTIL                                                          669

SEQ ID NO: 15           moltype = AA  length = 684
FEATURE                 Location/Qualifiers
REGION                  1..684
                        note = Synthetic construct
source                  1..684
                        mol_type = protein
                        organism = synthetic construct
SEQUENCE: 15
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA ATSELDCQQG  240
TRALLQTLGN LGYRASAKKA QICQKQVKYL GYLLKEGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
VKDAGKLTLG QPLTILTSHP VEALVRQPPN KWLSNARMTH YQAMLLDAER VHFGPTVSLN  480
PATLLPLPSG KPPRLSPDLA ETMAQTDLTD QPLPDADLTW YTGGSSFIRN GERKAGAAVT  540
TESEVIWAAS LPPGTSAQRA ELIALTQALK MAKGKKLTVY TDSRYAFATA HVHGEIYRRR  600
GWLTSKGKEI KNKNEILALL EALFLPKRLS IIHCPGHQKG DSPQAKGNRL ADDTAKKAAT  660
ETQSSLTILP TELIEGPKRP PWEY                                         684

SEQ ID NO: 16           moltype = AA  length = 669
FEATURE                 Location/Qualifiers
REGION                  1..669
                        note = Synthetic construct
source                  1..669
                        mol_type = protein
                        organism = synthetic construct
SEQUENCE: 16
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA ATSELDCQQG  240
TRALLQTLGN LGYRASAKKA QICQKQVKYL GYLLKEGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
```

-continued

```
VKDAGKLTLG QPLTILTSHP VEALVRQPPN KWLSNARMTH YQAMLLDAER VHFGPTVSLN  480
PATLLPLPSG KPPRLSPDLA ETMAQTDLTD QPLPDADLTW YTGGSSFIRN GERKAGAAVT  540
TESEVIWAAS LPPGTSAQRA ELIALTQALK MAKGKKLTVY TDSRYAFATA HVHGEIYRRR  600
GWLTSKGKEI KNKNEILALL EALFLPKRLS IIHCPGHQKG DSPQAKGNRL ADDTAKKAAT  660
ETQSSLTIL                                                          669

SEQ ID NO: 17          moltype = AA  length = 669
FEATURE                Location/Qualifiers
REGION                 1..669
                       note = Synthetic construct
source                 1..669
                       mol_type = protein
                       organism = synthetic construct
SEQUENCE: 17
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA AATRTECLEG  240
TKALLETLGN KGYRASAKKA QICLQEVTYL GYSLKDGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
VKDAGKLTLG QPLTILTSHP VEALVRQPPN KWLSNARMTH YQAMLLDAER VHFGPTVSLN  480
PATLLPLPSG KPPRLSPDLA ETMAQTDLTD QPLPDADLTW YTGGSSFIRN GERKAGAAVT  540
TESEVIWAAS LPPGTSAQRA ELIALTQALK MAKGKKLTVY TDSRYAFATA HVHGEIYRRR  600
GWLTSKGKEI KNKNEILALL EALFLPKRLS IIHCPGHQKG DSPQAKGNRL ADDTAKKAAT  660
ETQSSLTIL                                                          669

SEQ ID NO: 18          moltype = AA  length = 669
FEATURE                Location/Qualifiers
REGION                 1..669
                       note = Synthetic construct
source                 1..669
                       mol_type = protein
                       organism = synthetic construct
SEQUENCE: 18
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGL PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA AATRTECLEG  240
TKALLETLGN KGYRASAKKA QICLQEVTYL GYSLKDGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
VKDAGKLTLG QPLTILTSHP VEALVRQPPN KWLSNARMTH YQAMLLDAER VHFGPTVSLD  480
PATLLPLPSG KPPRLSPDLA ETMAQTDLTD QPLPDADLTW YTDGSSFIRN GERKAGAAVT  540
TESEVIWAAS LPPGTSAQRA ELIALTQALK MAKGKKLTVY TDSRYAFATA HVKGEIYRRR  600
GWLTSEGKEI KNKNEILALL EALFLPKRLS IIHCPGHQKG DSPQAKGNRL ADDTAKKAAT  660
ETQSSLTIL                                                          669

SEQ ID NO: 19          moltype = AA  length = 447
FEATURE                Location/Qualifiers
REGION                 1..447
                       note = Synthetic construct
source                 1..447
                       mol_type = protein
                       organism = synthetic construct
SEQUENCE: 19
YVDDLLLAAA TRTECLEGTK ALLETLGNKG YRASAKKAQI CLQEVTYLGY SLKDGQRWLT  60
KARKEAILSI PVPKNPRQVR EFLGTAGYCR LWIPGFAELA APLYPLTRPG TLFQWGTEQQ  120
LAFENIRKAL LSSPALGLPD ITKPFELFID ENSGFAKGVL VQKLGPWKRP VAYLSKKLDT  180
VASGWPPCLR MVAAIAILVK DAGKLTLGQP LTILTSHPVE ALVRQPPNKW LSNARMTHYQ  240
AMLLDAERVH FGPTVSLNPA TLLPLPSGKP PRLSPDLAET MAQTDLTDQP LPDADLTWYT  300
GGSSFIRNGE RKAGAAVTTE SEVIWAASLP PGTSAQRAEL IALTQALKMA KGKKLTVYTD  360
SRYAFATAHV HGEIYRRRGW LTSEGKEIKN KNEILALLEA LFLPKRLSII HCPGHQKGDS  420
PQAKGNRLAN DTAKKAATET QSSLTIL                                      447

SEQ ID NO: 20          moltype = AA  length = 692
FEATURE                Location/Qualifiers
REGION                 1..692
                       note = Synthetic construct
source                 1..692
                       mol_type = protein
                       organism = synthetic construct
SEQUENCE: 20
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGP PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA ATSELDCQQG TRALLQTLGN LGYRASAKKA QICQKQVKYL GYLLKEGQRW  300
LTKARKEAIL SIPVPKNPRQ VREFLGTAGY CRLWIPGFAE LAAPLYPLTR PGTLFQWGTE  360
```

-continued

```
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLN PATLLPLPSG KPPRLSPDLA ETMAQTDLTD QPLPDADLTW  540
YTAGSSIIRN GERKAGAAVT TESEVIWAAS LPPGTSAQRA ELIALTQALK MAKGKKLTVY  600
TDSRYAFATA HVHGEIYRRR GLLTSEGKEI KNKNEILALL EALFLPKRLS IIYCPGHQKG  660
DSPQAKGNRL ADDTAKKAAT ETQSSLTILA AA                                692

SEQ ID NO: 21          moltype = AA  length = 707
FEATURE                Location/Qualifiers
REGION                 1..707
                       note = Synthetic construct
source                 1..707
                       mol_type = protein
                       organism = synthetic construct
SEQUENCE: 21
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGP PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA ATSELDCQQG TRALLQTLGN LGYRASAKKA QICQKQVKYL GYLLKEGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLN PATLLPLPSG KPPRLSPDLA ETMAQTDLTD QPLPDADLTW  540
YTGGSSFIRN GERKAGAAVT TESEVIWAAS LPPGTSAQRA ELIALTQALK MAKGKKLTVY  600
TDSRYAFATA HVHGEIYRRR GWLTSKGKEI KNKNEILALL EALFLPKRLS IIHCPGHQKG  660
DSPQAKGNRL ADDTAKKAAT ETQSSLTILP TELIEGPKRP PWEYAAA                707

SEQ ID NO: 22          moltype = AA  length = 692
FEATURE                Location/Qualifiers
REGION                 1..692
                       note = Synthetic construct
source                 1..692
                       mol_type = protein
                       organism = synthetic construct
SEQUENCE: 22
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGP PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA ATSELDCQQG TRALLQTLGN LGYRASAKKA QICQKQVKYL GYLLKEGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLN PATLLPLPSG KPPRLSPDLA ETMAQTDLTD QPLPDADLTW  540
YTGGSSFIRN GERKAGAAVT TESEVIWAAS LPPGTSAQRA ELIALTQALK MAKGKKLTVY  600
TDSRYAFATA HVHGEIYRRR GWLTSKGKEI KNKNEILALL EALFLPKRLS IIHCPGHQKG  660
DSPQAKGNRL ADDTAKKAAT ETQSSLTILA AA                                692

SEQ ID NO: 23          moltype = AA  length = 692
FEATURE                Location/Qualifiers
REGION                 1..692
                       note = Synthetic construct
source                 1..692
                       mol_type = protein
                       organism = synthetic construct
SEQUENCE: 23
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGP PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA AATRTECLEG TKALLETLGN KGYRASAKKA QICLQEVTYL GYSLKDGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLN PATLLPLPSG KPPRLSPDLA ETMAQTDLTD QPLPDADLTW  540
YTGGSSFIRN GERKAGAAVT TESEVIWAAS LPPGTSAQRA ELIALTQALK MAKGKKLTVY  600
TDSRYAFATA HVHGEIYRRR GWLTSKGKEI KNKNEILALL EALFLPKRLS IIHCPGHQKG  660
DSPQAKGNRL ADDTAKKAAT ETQSSLTILA AA                                692

SEQ ID NO: 24          moltype = AA  length = 692
FEATURE                Location/Qualifiers
REGION                 1..692
                       note = Synthetic construct
source                 1..692
                       mol_type = protein
                       organism = synthetic construct
SEQUENCE: 24
MGSSHHHHHH SSGLVPRGSH MTLNIEDEYR LHETSKEPDV SLGSTWLSDF PQAWAETGGM  60
```

-continued

```
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGL PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA AATRTECLEG TKALLETLGN KGYRASAKKA QICLQEVTYL GYSLKDGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLD PATLLPLPSG KPPRLSPDLA ETMAQTDLTD QPLPDADLTW  540
YTDGSSFIRN GERKAGAAVT TESEVIWAAS LPPGTSAQRA ELIALTQALK MAKGKKLTVY  600
TDSRYAFATA HVKGEIYRRR GWLTSEGKEI KNKNEILALL EALFLPKRLS IIHCPGHQKG  660
DSPQAKGNRL ADDTAKKAAT ETQSSLTILA AA                               692

SEQ ID NO: 25          moltype = AA  length = 692
FEATURE                Location/Qualifiers
REGION                 1..692
                       note = Synthetic construct
source                 1..692
                       mol_type = protein
                       organism = synthetic construct
SEQUENCE: 25
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGL PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA AATRTECLEG TKALLETLGN KGYRASAKKA QICLQEVTYL GYSLKDGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLN PATLLPLPSG KPPRLSPDLA ETMAQTDLTD QPLPDADLTW  540
YTGGSSFIRN GERKAGAAVT TESEVIWAAS LPPGTSAQRA ELIALTQALK MAKGKKLTVY  600
TDSRYAFATA HVHGEIYRRR GWLTSEGKEI KNKNEILALL EALFLPKRLS IIHCPGHQKG  660
DSPQAKGNRL ANDTAKKAAT ETQSSLTILA AA                               692

SEQ ID NO: 26          moltype = AA  length = 279
FEATURE                Location/Qualifiers
REGION                 1..279
                       note = Feline Leukemia Virus
source                 1..279
                       mol_type = protein
                       organism = unidentified
SEQUENCE: 26
MTLQLEEEYR LFEPESTQKQ EMDIWLKNFP QAWAETGGMG MAHCQAPVLI QLKATATPIS  60
IRQYPMPHEA YQGIKPHIRR MLDQGILKPC QSPWNTPLLP VKKPGTKDYR PVQDLREVNK  120
RVEDIHPTVP NPYNLLSTLP PSHPWYTVLD LKDAFFCLRL HSESQLLFAF EWRDPEIGLS  180
GQLTWTRLPQ GFKNSPTLFD EALHSDLADF RVRYPALVLL QYVDDLLLAA ATRTECLEGT  240
KALLETLGNK GYRASAKKAQ ICLQEVTYLG YSLKDGQRW                        279

SEQ ID NO: 27          moltype = AA  length = 497
FEATURE                Location/Qualifiers
REGION                 1..497
                       note = Feline Leukemia Virus
source                 1..497
                       mol_type = protein
                       organism = unidentified
SEQUENCE: 27
MTLQLEEEYR LFEPESTQKQ EMDIWLKNFP QAWAETGGMG MAHCQAPVLI QLKATATPIS  60
IRQYPMPHEA YQGIKPHIRR MLDQGILKPC QSPWNTPLLP VKKPGTKDYR PVQDLREVNK  120
RVEDIHPTVP NPYNLLSTLP PSHPWYTVLD LKDAFFCLRL HSESQLLFAF EWRDPEIGLS  180
GQLTWTRLPQ GFKNSPTLFD EALHSDLADF RVRYPALVLL QYVDDLLLAA ATRTECLEGT  240
KALLETLGNK GYRASAKKAQ ICLQEVTYLG YSLKDGQRWL TKARKEAILS IPVPKNPRQV  300
REFLGTAGYC RLWIPGFAEL AAPLYPLTRP GTLFQWGTEQ QLAFENIRKA LLSSPALGLP  360
DITKPFELFI DENSGFAKGV LVQKLGPWKR PVAYLSKKLD TVASGWPPCL RMVAAIAILV  420
KDAGKLTLGQ PLTILTSHPV EALVRQPPNK WLSNARMTHY QAMLLDAERV HFGPTVSLNP  480
ATLLPLPSGK PPRLSPD                                                497

SEQ ID NO: 28          moltype = AA  length = 392
FEATURE                Location/Qualifiers
REGION                 1..392
                       note = Mouse Leukemia Virus
source                 1..392
                       mol_type = protein
                       organism = unidentified
SEQUENCE: 28
LTEARKETVM GQPTPKTPRQ LREFLGTAGF CRLWIPGFAE MAAPLYPLTK TGTLFNWGPD  60
QQKAYQEIKQ ALLTAPALGL PDLTKPFELF VDEKQGYAKG VLTQKLGPWR RPVAYLSKKL  120
DPVAAGWPPC LRMVAAIAVL TKDAGKLTMG QPLVILAPHA VEALVKQPPD RWLSNARMTH  180
YQALLLDTDR VQFGPVVALN PATLLPLPEE GLQHDCLDIL AEAHGTRSDL TDQPLPDADH  240
TWYTDGSSFL QEGQRKAGAA VTTETEVIWA RALPAGTSAQ RAELIALTQA LKMAEGKKLN  300
VYTDSRYAFA TAHIHGEIYR RRGLLTSEGK EIKNKDEILA LLKALFLPKR LSIIHCPGHQ  360
```

-continued

```
KGNSAEARGN RMADQAAREV ATRETPGTST LL                             392

SEQ ID NO: 29           moltype = AA  length = 174
FEATURE                 Location/Qualifiers
REGION                  1..174
                        note = Mouse Leukemia Virus
source                  1..174
                        mol_type = protein
                        organism = unidentified
SEQUENCE: 29
ILAEAHGTRS DLTDQPLPDA DHTWYTDGSS FLQEGQRKAG AAVTTETEVI WARALPAGTS  60
AQRAELIALT QALKMAEGKK LNVYTDSRYA FATAHIHGEI YRRRGLLTSE GKEIKNKDEI  120
LALLKALFLP KRLSIIHCPG HQKGNSAEAR GNRMADQAAR EVATRETPGT STLL        174

SEQ ID NO: 30           moltype = AA  length = 671
FEATURE                 Location/Qualifiers
REGION                  1..671
                        note = Synthetic construct
source                  1..671
                        mol_type = protein
                        organism = synthetic construct
SEQUENCE: 30
MTLQLEEEYR LFEPESTQKQ EMDIWLKNFP QAWAETGGMG MAHCQAPVLI QLKATATPIS  60
IRQYPMPHEA YQGIKPHIRR MLDQGILKPC QSPWNTPLLP VKKPGTKDYR PVQDLREVNK  120
RVEDIHPTVP NPYNLLSTLP PSHPWYTVLD LKDAFFCLRL HSESQLLFAF EWRDPEIGLS  180
GQLTWTRLPQ GFKNSPTLFD EALHSDLADF RVRYPALVLL QYVDDLLLAA ATRTECLEGT  240
KALLETLGNK GYRASAKKAQ ICLQEVTYLG YSLKDGQRWL TEARKETVMG QPTPKTPRQL  300
REFLGTAGFC RLWIPGFAEM AAPLYPLTKT GTLFNWGPDQ QKAYQEIKQA LLTAPALGLP  360
DLTKPFELFV DEKQGYAKGV LTQKLGPWRR PVAYLSKKLD PVAAGWPPCL RMVAAIAVLT  420
KDAGKLTMGQ PLVILAPHAV EALVKQPPDR WLSNARMTHY QALLLDTDRV QFGPVVALNP  480
ATLLPLPEEG LQHDCLDILA EAHGTRSDLT DQPLPDADHT WYTDGSSFLQ EGQRKAGAAV  540
TTETEVIWAR ALPAGTSAQR AELIALTQAL KMAEGKKLNV YTDSRYAFAT AHIHGEIYRR  600
RGLLTSEGKE IKNKDEILAL LKALFLPKRL SIIHCPGHQK GNSAEARGNR MADQAAREVA  660
TRETPGTSTL L                                                    671

SEQ ID NO: 31           moltype = AA  length = 671
FEATURE                 Location/Qualifiers
REGION                  1..671
                        note = Synthetic construct
source                  1..671
                        mol_type = protein
                        organism = synthetic construct
SEQUENCE: 31
MTLQLEEEYR LFEPESTQKQ EMDIWLKNFP QAWAETGGMG MAHCQAPVLI QLKATATPIS  60
IRQYPMPHEA YQGIKPHIRR MLDQGILKPC QSPWNTPLLP VKKPGTKDYR PVQDLREVNK  120
RVEDIHPTVP NPYNLLSTLP PSHPWYTVLD LKDAFFCLRL HSESQLLFAF EWRDPEIGLS  180
GQLTWTRLPQ GFKNSPTLFD EALHSDLADF RVRYPALVLL QYVDDLLLAA ATRTECLEGT  240
KALLETLGNK GYRASAKKAQ ICLQEVTYLG YSLKDGQRWL TKARKEAILS IPVPKNPRQV  300
REFLGTAGYC RLWIPGFAEL AAPLYPLTRP GTLFQWGTEQ QLAFENIRKA LLSSPALGLP  360
DITKPFELFI DENSGFAKGV LVQKLGPWKR PVAYLSKKLD TVASGWPPCL RMVAAIAILV  420
KDAGKLTLGQ PLTILTSHPV EALVRQPPNK WLSNARMTHY QAMLLDAERV HFGPTVSLNP  480
ATLLPLPSGK PPRLSPDILA EAHGTRSDLT DQPLPDADHT WYTDGSSFLQ EGQRKAGAAV  540
TTETEVIWAR ALPAGTSAQR AELIALTQAL KMAEGKKLNV YTDSRYAFAT AHIHGEIYRR  600
RGLLTSEGKE IKNKDEILAL LKALFLPKRL SIIHCPGHQK GNSAEARGNR MADQAAREVA  660
TRETPGTSTL L                                                    671

SEQ ID NO: 32           moltype = AA  length = 671
FEATURE                 Location/Qualifiers
REGION                  1..671
                        note = Mouse Leukemia Virus
source                  1..671
                        mol_type = protein
                        organism = unidentified
SEQUENCE: 32
TLNIEDEHRL HETSKEPDVS LGSTWLSDFP QAWAETGGMG LAVRQAPLII PLKATSTPVS  60
IKQYPMSQEA RLGIKPHIQR LLDQGILVPC QSPWNTPLLP VKKPGTNDYR PVQDLREVNK  120
RVEDIHPTVP NPYNLLSGLP PSHQWYTVLD LKDAFFCLRL HPTSQPLFAF EWRDPEMGIS  180
GQLTWTRLPQ GFKNSPTLFD EALHRDLADF RIQHPDLILL QYVDDLLLAA TSELDCQQGT  240
RALLQTLGNL GYRASAKKAQ ICQKQVKYLG YLLKEGQRWL TEARKETVMG QPTPKTPRQL  300
REFLGTAGFC RLWIPGFAEM AAPLYPLTKT GTLFNWGPDQ QKAYQEIKQA LLTAPALGLP  360
DLTKPFELFV DEKQGYAKGV LTQKLGPWRR PVAYLSKKLD PVAAGWPPCL RMVAAIAVLT  420
KDAGKLTMGQ PLVILAPHAV EALVKQPPDR WLSNARMTHY QALLLDTDRV QFGPVVALNP  480
ATLLPLPEEG LQHNCLDILA EAHGTRPDLT DQPLPDADHT WYTDGSSLLQ EGQRKAGAAV  540
TTETEVIWAK ALPAGTSAQR AELIALTQAL KMAEGKKLNV YTDSRYAFAT AHIHGEIYRR  600
RGLLTSEGKE IKNKDEILAL LKALFLPKRL SIIHCPGHQK GHSAEARGNR MADQAARKAA  660
ITETPDTSTL L                                                    671

SEQ ID NO: 33           moltype = AA  length = 667
FEATURE                 Location/Qualifiers
```

```
REGION                  1..667
                        note = Feline Leukemia Virus
source                  1..667
                        mol_type = protein
                        organism = unidentified
SEQUENCE: 33
TLQLEEEYRL FEPESTQKQE MDIWLKNFPQ AWAETGGMGM AHCQAPVLIQ LKATATPISI  60
RQYPMPHEAY QGIKPHIRRM LDQGILKPCQ SPWNTPLLPV KKPGTKDYRP VQDLREVNKR  120
VEDIHPTVPN PYNLLSTLPP SHPWYTVLDL KDAFFCLRLH SESQLLFAFE WRDPEIGLSG  180
QLTWTRLPQG FKNSPTLFDE ALHSDLADFR VRYPALVLLQ YVDDLLLAAA TRTECLEGTK  240
ALLETLGNKG YRASAKKAQI CLQEVTYLGY SLKDGQRWLT KARKEAILSI PVPKNPRQVR  300
EFLGTAGYCR LWIPGFAELA APLYPLTRPG TLFQWGTEQQ LAFENIRKAL LSSPALGLPD  360
ITKPFELFID ENSGFAKGVL VQKLGPWKRP VAYLSKKLDT VASGWPPCLR MVAAIAILVK  420
DAGKLTLGQP LTILTSHPVE ALVRQPPNKW LSNARMTHYQ AMLLDAERVH FGPTVSLNPA  480
TLLPLPSGKP PRLSPDLAET MAQTDLTDQP LPDADLTWYT DGSSFIRNGE RKAGAAVTTE  540
SEVIWAASLP PGTSAQRAEL IALTQALKMA KGKKLTVYTD SRYAFATAHV HGEIYRRRGL  600
LTSEGKEIKN KNEILALLEA LFLPKRLSII HCPGHQKGDS PQAKGNRLAD DTAKKAATET  660
QSSLTIL                                                          667

SEQ ID NO: 34           moltype = AA  length = 684
FEATURE                 Location/Qualifiers
REGION                  1..684
                        note = Synthetic construct
source                  1..684
                        mol_type = protein
                        organism = synthetic construct
SEQUENCE: 34
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA ATSELDCQQG  240
TRALLQTLGN LGYRASAKKA QICQKQVKYL GYLLKEGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
VKDAGKLTLG QPLTILTSHP VEALVRQPPN KWLSNARMTH YQAMLLDAER VHFGPTVSLN  480
PATLLPLPSG KPPRLSPDLA ETMAQTDLTD QPLPDADLTW YTAGSSIIRN GERKAGAAVT  540
TESEVIWAAS LPPGTSAQRA ELIALTQALK MAKGKKLTVY TDSRYAFATA HVHGEIYRRR  600
GLLTSEGKEI KNKNEILALL EALFLPKRLS IIYCPGHQKG DSPQAKGNRL ADDTAKKAAT  660
ETQSSLTILP TELIEGPKRP PWEY                                       684

SEQ ID NO: 35           moltype = AA  length = 684
FEATURE                 Location/Qualifiers
REGION                  1..684
                        note = Synthetic construct
source                  1..684
                        mol_type = protein
                        organism = synthetic construct
SEQUENCE: 35
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA AATRTECLEG  240
TKALLETLGN KGYRASAKKA QICLQEVTYL GYSLKDGQRW LTKARKEAIL SIPVPKNPRQ  300
VREFLGTAGY CRLWIPGFAE LAAPLYPLTR PGTLFQWGTE QQLAFENIRK ALLSSPALGL  360
PDITKPFELF IDENSGFAKG VLVQKLGPWK RPVAYLSKKL DTVASGWPPC LRMVAAIAIL  420
VKDAGKLTLG QPLTILTSHP VEALVRQPPN KWLSNARMTH YQAMLLDAER VHFGPTVSLN  480
PATLLPLPSG KPPRLSPDLA ETMAQTDLTD QPLPDADLTW YTGGSSFIRN GERKAGAAVT  540
TESEVIWAAS LPPGTSAQRA ELIALTQALK MAKGKKLTVY TDSRYAFATA HVHGEIYRRR  600
GWLTSKGKEI KNKNEILALL EALFLPKRLS IIHCPGHQKG DSPQAKGNRL ADDTAKKAAT  660
ETQSSLTILP TELIEGPKRP PWEY                                       684

SEQ ID NO: 36           moltype = AA  length = 278
FEATURE                 Location/Qualifiers
REGION                  1..278
                        note = Synthetic construct
source                  1..278
                        mol_type = protein
                        organism = synthetic construct
SEQUENCE: 36
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQYVDDLLLA ATSELDCQQG  240
TRALLQTLGN LGYRASAKKA QICQKQVKYL GYLLKEGQ                        278

SEQ ID NO: 37           moltype = AA  length = 406
FEATURE                 Location/Qualifiers
REGION                  1..406
                        note = Synthetic construct
```

-continued

```
source                  1..406
                        mol_type = protein
                        organism = synthetic construct
SEQUENCE: 37
RWLTKARKEA ILSIPVPKNP RQVREFLGTA GYCRLWIPGF AELAAPLYPL TRPGTLFQWG  60
TEQQLAFENI RKALLSSPAL GLPDITKPFE LFIDENSGFA KGVLVQKLGP WKRPVAYLSK  120
KLDTVASGWP PCLRMVAAIA ILVKDAGKLT LGQPLTILTS HPVEALVRQP PNKWLSNARM  180
THYQAMLLDA ERVHFGPTVS LNPATLLPLP SGKPPRLSPD LAETMAQTDL TDQPLPDADL  240
TWYTAGSSII RNGERKAGAA VTTESEVIWA ASLPPGTSAQ RAELIALTQA LKMAKGKKLT  300
VYTDSRYAFA TAHVHGEIYR RRGLLTSEGK EIKNKNEILA LLEALFLPKR LSIIYCPGHQ  360
KGDSPQAKGN RLADDTAKKA ATETQSSLTI LPTELIEGPK RPPWEY                406

SEQ ID NO: 38           moltype = AA  length = 222
FEATURE                 Location/Qualifiers
REGION                  1..222
                        note = Synthetic construct
source                  1..222
                        mol_type = protein
                        organism = synthetic construct
SEQUENCE: 38
MTLNIEDEYR LHETSKEPDV SLGSTWLSDF PQAWAETGGM GLAVRQAPLI IPLKATSTPV  60
SIKQYPMSQE ARLGIKPHIQ RLLDQGILVP CQSPWNTPLL PVKKPGTNDY RPVQDLREVN  120
KRVEDIHPTV PNPYNLLSGP PPSHQWYTVL DLKDAFFCLR LHPTSQPLFA FEWRDPEMGI  180
SGQLTWTRLP QGFKNSPTLF NEALHRDLAD FRIQHPDLIL LQ                    222

SEQ ID NO: 39           moltype = AA  length = 462
FEATURE                 Location/Qualifiers
REGION                  1..462
                        note = Synthetic construct
source                  1..462
                        mol_type = protein
                        organism = synthetic construct
SEQUENCE: 39
YVDDLLLAAA TRTECLEGTK ALLETLGNKG YRASAKKAQI CLQEVTYLGY SLKDGQRWLT  60
KARKEAILSI PVPKNPRQVR EFLGTAGYCR LWIPGFAELA APLYPLTRPG TLFQWGTEQQ  120
LAFENIRKAL LSSPALGLPD ITKPFELFID ENSGFAKGVL VQKLGPWKRP VAYLSKKLDT  180
VASGWPPCLR MVAAIAILVK DAGKLTLGQP LTILTSHPVE ALVRQPPNKW LSNARMTHYQ  240
AMLLDAERVH FGPTVSLNPA TLLPLPSGKP PRLSPDLAET MAQTDLTDQP LPDADLTWYT  300
GGSSFIRNGE RKAGAAVTTE SEVIWAASLP PGTSAQRAEL IALTQALKMA KGKKLTVYTD  360
SRYAFATAHV HGEIYRRRGW LTSKGKEIKN KNEILALLEA LFLPKRLSII HCPGHQKGDS  420
PQAKGNRLAD DTAKKAATET QSSLTILPTE LIEGPKRPPW EY                    462

SEQ ID NO: 40           moltype = AA  length = 707
FEATURE                 Location/Qualifiers
REGION                  1..707
                        note = Synthetic construct
source                  1..707
                        mol_type = protein
                        organism = synthetic construct
SEQUENCE: 40
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGP PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA ATSELDCQQG TRALLQTLGN LGYRASAKKA QICQKQVKYL GYLLKEGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
YQAMLLDAER VHFGPTVSLN PATLLPLPSG KPPRLSPDLA ETMAQTDLTD QPLPDADLTW  540
YTAGSSIIRN GERKAGAAVT TESEVIWAAS LPPGTSAQRA ELIALTQALK MAKGKKLTVY  600
TDSRYAFATA HVHGEIYRRR GLLTSEGKEI KNKNEILALL EALFLPKRLS IIYCPGHQKG  660
DSPQAKGNRL ADDTAKKAAT ETQSSLTILP TELIEGPKRP PWEYAAA               707

SEQ ID NO: 41           moltype = AA  length = 707
FEATURE                 Location/Qualifiers
REGION                  1..707
                        note = Synthetic construct
source                  1..707
                        mol_type = protein
                        organism = synthetic construct
SEQUENCE: 41
MGSSHHHHHH SSGLVPRGSH MTLNIEDEYR LHETSKEPDV SLGSTWLSDF PQAWAETGGM  60
GLAVRQAPLI IPLKATSTPV SIKQYPMSQE ARLGIKPHIQ RLLDQGILVP CQSPWNTPLL  120
PVKKPGTNDY RPVQDLREVN KRVEDIHPTV PNPYNLLSGP PPSHQWYTVL DLKDAFFCLR  180
LHPTSQPLFA FEWRDPEMGI SGQLTWTRLP QGFKNSPTLF NEALHRDLAD FRIQHPDLIL  240
LQYVDDLLLA AATRTECLEG TKALLETLGN KGYRASAKKA QICLQEVTYL GYSLKDGQRW  300
LTKARKEAIL SIPVPKNPRQ VREFLGTAGY CRLWIPGFAE LAAPLYPLTR PGTLFQWGTE  360
QQLAFENIRK ALLSSPALGL PDITKPFELF IDENSGFAKG VLVQKLGPWK RPVAYLSKKL  420
DTVASGWPPC LRMVAAIAIL VKDAGKLTLG QPLTILTSHP VEALVRQPPN KWLSNARMTH  480
```

-continued

```
YQAMLLDAER VHFGPTVSLN PATLLPLPSG KPPRLSPDLA ETMAQTDLTD QPLPDADLTW  540
YTGGSSFIRN GERKAGAAVT TESEVIWAAS LPPGTSAQRA ELIALTQALK MAKGKKLTVY  600
TDSRYAFATA HVHGEIYRRR GWLTSKGKEI KNKNEILALL EALFLPKRLS IIHCPGHQKG  660
DSPQAKGNRL ADDTAKKAAT ETQSSLTILP TELIEGPKRP PWEYAAA                707

SEQ ID NO: 42          moltype = AA  length = 8
FEATURE                Location/Qualifiers
REGION                 1..8
                       note = Synthetic construct
source                 1..8
                       mol_type = protein
                       organism = synthetic construct
SEQUENCE: 42
DYKDDDDK                                                           8
```

What is claimed is:

1. A nucleic acid comprising a polynucleotide encoding a hybrid reverse transcriptase, the hybrid reverse transcriptase comprising a finger domain, a palm domain, a thumb domain, a connection domain and an RNase H domain, wherein (A) the hybrid reverse transcriptase comprises:

(i) a portion of feline leukemia virus reverse transcriptase (FLVRT) comprising the finger domain and the palm domain, wherein the portion of the FLVRT is at least 95% identical to SEQ ID NO:26, said portion of the FLVRT linked to a portion of mouse leukemia virus reverse transcriptase (MLVRT) comprising the thumb domain, the connection domain, and the RNase H domain, wherein the portion of the MLVRT is at least 95% identical to SEQ ID NO:28; or (ii) a portion of feline leukemia virus reverse transcriptase (FLVRT) comprising the finger domain, the palm domain, the thumb domain, and the connection domain wherein the portion of the FLVRT is at least 95% identical to SEQ ID NO:27, said portion of the FLVRT linked to a portion of mouse leukemia virus reverse transcriptase (MLVRT) comprising the RNase H domain, wherein the portion of the MLVRT is at least 95% identical to SEQ ID NO:29; or (B) the hybrid reverse transcriptase comprises:

a portion of mouse leukemia virus reverse transcriptase (MLVRT) comprising the finger domain and the palm domain, wherein the portion of the MLVRT is at least 95% identical to SEQ ID NO:1, said portion of the MLVRT linked to a portion of feline leukemia virus reverse transcriptase (FLVRT) comprising the thumb domain, the connection domain, and the RNase H domain, wherein the portion of the FLVRT is at least 95% identical to SEQ ID NO:5.

2. The nucleic acid of claim 1, comprising a portion of feline leukemia virus reverse transcriptase (FLVRT) comprising the finger domain and the palm domain, wherein the portion of the FLVRT is at least 95% identical to SEQ ID NO:26, said portion of the FLVRT linked to a portion of mouse leukemia virus reverse transcriptase (MLVRT) comprising the thumb domain, the connection domain, and the RNase H domain, wherein the portion of the MLVRT is at least 95% identical to SEQ ID NO:28.

3. The nucleic acid of claim 2, wherein the hybrid reverse transcriptase comprises SEQ ID NO:30.

4. The nucleic acid of claim 1, a portion of feline leukemia virus reverse transcriptase (FLVRT) comprising the finger domain, the palm domain, the thumb domain, and the connection domain wherein the portion of the FLVRT is at least 95% identical to SEQ ID NO:27, said portion of the FLVRT linked to a portion of mouse leukemia virus reverse transcriptase (MLVRT) comprising the RNase H domain, wherein the portion of the MLVRT is at least 95% identical to SEQ ID NO:29.

5. The nucleic acid of claim 4, wherein the hybrid reverse transcriptase comprises SEQ ID NO:31.

6. The nucleic acid of claim 1, having at least one mutation that improves thermostability.

7. The nucleic acid of claim 1, wherein the hybrid reverse transcriptase comprises:

a portion of mouse leukemia virus reverse transcriptase (MLVRT) comprising the finger domain and the palm domain, wherein the portion of the MLVRT is at least 95% identical to SEQ ID NO:1, said portion of the MLVRT linked to a portion of feline leukemia virus reverse transcriptase (FLVRT) comprising the thumb domain, the connection domain, and the RNase H domain, wherein the portion of the FLVRT is at least 95% identical to SEQ ID NO:5.

8. The nucleic acid of claim 7, wherein the portion of the MLVRT comprises SEQ ID NO:1 and the portion of the FLVRT comprises SEQ ID NO:5.

9. The nucleic acid of claim 8, wherein the portion of the FLVRT comprises SEQ ID NO:6 or SEQ ID NO:10.

10. The nucleic acid of claim 9, wherein the portion of the FLVRT comprises SEQ ID NO:7, SEQ ID NO:8, SEQ ID NO:9, or SEQ ID NO:11.

11. The nucleic acid of claim 8, wherein the portion of the MLVRT comprises SEQ ID NO:2.

12. The nucleic acid of claim 8, wherein the portion of the MLVRT comprises SEQ ID NO:3 or SEQ ID NO:4.

13. The nucleic acid of claim 8, wherein:

the portion of the MLVRT comprises SEQ ID NO:4 and the portion of the FLVRT comprises SEQ ID NO:7; or the portion of the MLVRT comprises SEQ ID NO:4 and the portion of the FLVRT comprises SEQ ID NO:8; or the portion of the MLVRT comprises SEQ ID NO:4 and the portion of the FLVRT comprises SEQ ID NO:9; or the portion of the MLVRT comprises SEQ ID NO:3 and the portion of the FLVRT comprises SEQ ID NO:11; or the portion of the MLVRT comprises SEQ ID NO:3 and the portion of the FLVRT comprises SEQ ID NO:10; or the portion of the MLVRT comprises SEQ ID NO:4 and the portion of the FLVRT comprises SEQ ID NO:13.

14. The nucleic acid of claim 8, wherein the hybrid reverse transcriptase comprises a sequence at least 95% identical to SEQ ID NO: 14, 15, 16, 17, 18, 19, 34, or 35.

15. The nucleic acid of claim 1, comprising a promoter operably linked to the polynucleotide.

16. An expression vector comprising the nucleic acid of claim 1.

17. A cell comprising the nucleic acid of claim 1.

* * * * *